United States Patent
Kuzma

(10) Patent No.: US 6,195,586 B1
(45) Date of Patent: *Feb. 27, 2001

(54) SPACE-FILLING COCHLEAR ELECTRODE

(75) Inventor: Janusz A. Kuzma, Englewood, CO (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/298,410

(22) Filed: Apr. 23, 1999

Related U.S. Application Data

(63) Continuation-in-part of application No. 09/140,034, filed on Aug. 26, 1998, now Pat. No. 6,038,484, which is a continuation-in-part of application No. 09/216,063, filed on Dec. 18, 1998, now Pat. No. 6,078,841, which is a continuation-in-part of application No. 09/247,734, filed on Feb. 9, 1999.

(51) Int. Cl.⁷ ..................................................... A61N 1/05
(52) U.S. Cl. ............................................................. 607/137
(58) Field of Search ............................... 607/55–57, 136, 607/137; 600/585

(56) References Cited

U.S. PATENT DOCUMENTS 5,545,219 * 8/1996 Kuzma ................................. 607/137
5,653,742 * 8/1997 Parker et al. ......................... 607/137
6,038,484 * 3/2000 Kuzma ................................. 607/137

* cited by examiner

Primary Examiner—George R. Evanisko
(74) Attorney, Agent, or Firm—Bryant R. Gold

(57) ABSTRACT

An implantable space-filling electrode system, adapted for insertion into a cochlea, includes an elongate electrode array and a positioner. The electrode array has a multiplicity of electrode contacts carried on a flexible elongate carrier, which carrier is adapted for insertion into one of the spiraling ducts, e.g., the scala tympani, of the cochlea. The positioner is an elongate, flexible member, having a longitudinal channel that passes therethrough. The positioner is adapted to reside in and fill the space in the cochlear channel behind the electrode array so as to position and maintain the electrode array against a modiolar wall of the cochlea. A distal tip of the positioner is detachably joined to the electrode array at one point near the distal tip of the electrode array. To insert the electrode system into the cochlea, a stylet wire is inserted into the channel of the positioner, and the positioner is then gently guided and pushed into the cochlea by extending the stylet wire. As the positioner is thus inserted into the cochlea, the electrode array is carried along with it, thereby allowing both elements—the electrode array and the positioner—to be implanted within the cochlea during a single implant operation.

18 Claims, 15 Drawing Sheets

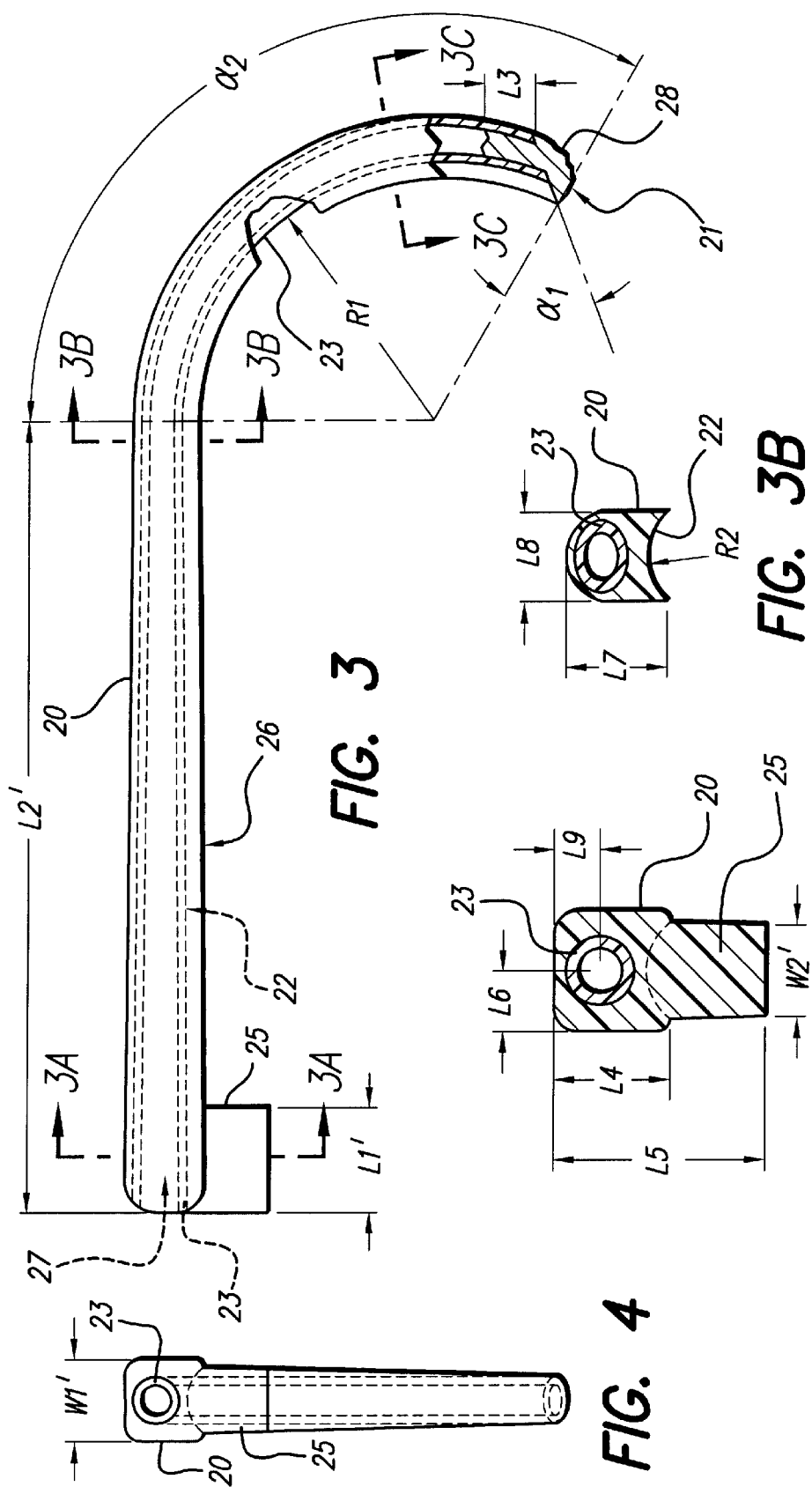

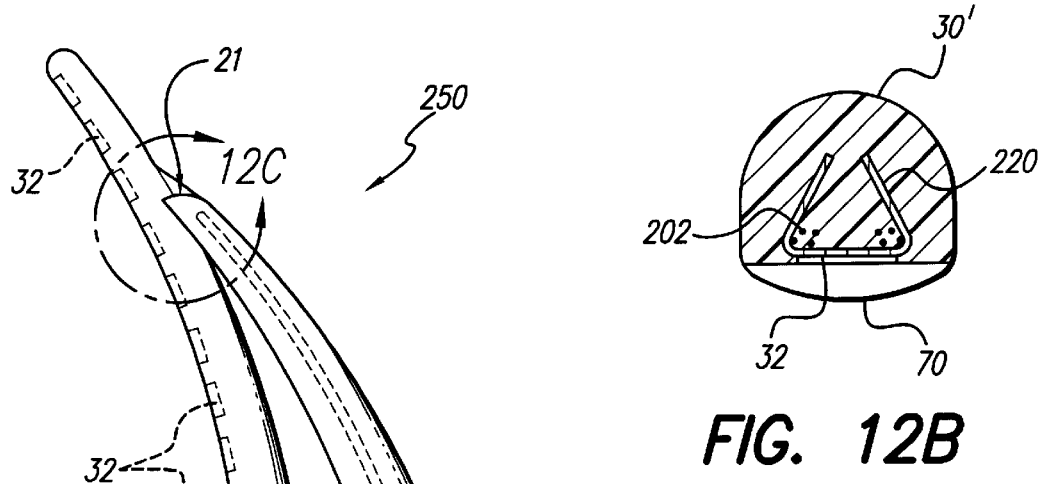
FIG. 12B
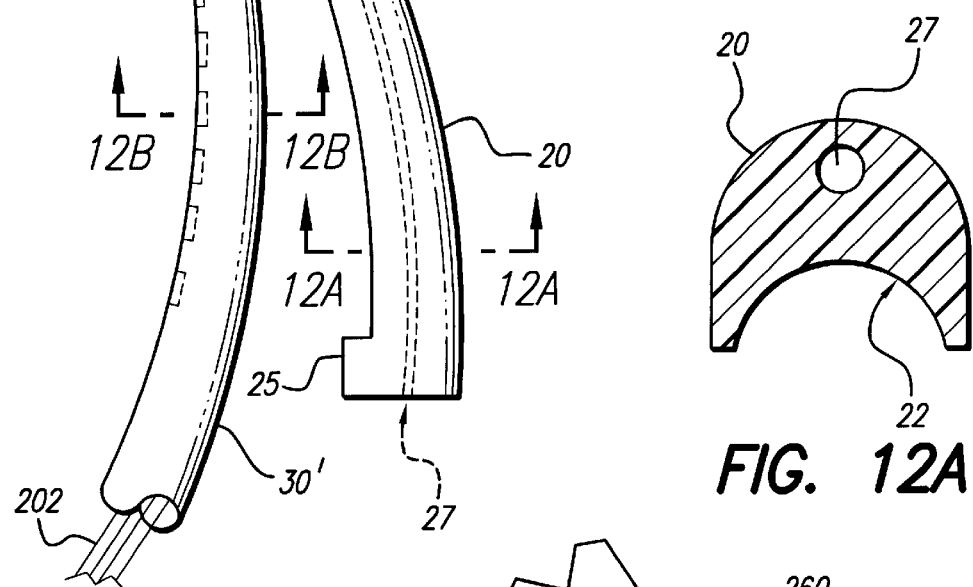
FIG. 12A
FIG. 12
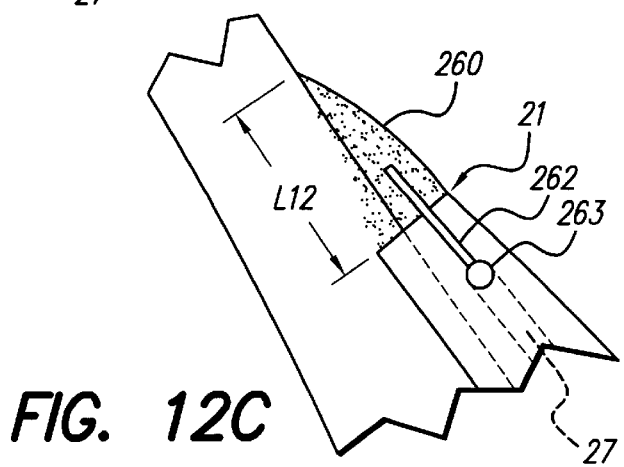
FIG. 12C

SPACE-FILLING COCHLEAR ELECTRODE

This application is a continuation-in-part (CIP) of U.S. Application Ser. No. 09/140,034, filed Aug. 26, 1998 now U.S. Pat. No. 6,038,484; U.S. application Ser. No. 09/216,063, filed Dec. 18, 1998 now U.S. Pat. No. 6,078,841; and U.S. application Ser. No. 09/247,734, filed Feb. 9, 1999; all of which patent applications are incorporated herein by reference.

BACKGROUND OF THE INVENTION

The present invention relates to implantable stimulation devices, e.g., cochlear prosthesis used to electrically stimulate the auditory nerve, and more particularly to an electrode array for use with a cochlear stimulator that is designed to hug the modiolus so as to place electrode contacts of the electrode array in close proximity to the ganglion cells and thereby to the auditory nerve fibers. Advantageously, such electrode array generally places the electrode contacts of the electrode array along one side of the array so that when the array is implanted within the cochlea, the side of the array whereon the electrode contacts are located can be positioned in close proximity to the ganglion cells that are to be stimulated, thereby allowing such ganglion cells to be stimulated with minimal power consumption. For example, where the array is implanted into the cochlea, the electrode side of the array may be positioned closest to the modiolar wall, thereby placing all of the individual electrode contacts in close proximity to the ganglion cells and thereby in close proximity to the auditory nerve fibers.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlea (the hair cells are located in the vicinity of the radially outer wall of the cochlea) by presenting electrical stimulation to the auditory nerve fibers directly, leading to the perception of sound in the brain and at least partial restoration of hearing function. The common denominator in most of these cochlear prosthesis systems has been the implantation into the cochlea of electrodes which are responsive to a suitable external source of electrical stimuli and which are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis performs the function of separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6–30 in number. Such electrode array is pushed into the scala tympani duct to a depth of about 20–30 mm via a surgical opening made in the round window at the basal end of the duct. During use, electrical current is passed into the fluids and tissues immediately surrounding the individual electrode contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site. Thus, there is a need for the electrode contacts to be positioned as close to the ganglion cells as possible. This means, in practice, that the electrode array, after implant, should preferably hug the modiolar wall, and that the individual electrodes of the electrode array should be positioned on or near that surface of the electrode array which is closest to the modiolar wall.

In order to address the above need, it is known in the art to make an intracochlear electrode array that includes a spiral-shaped resilient carrier which generally has a natural spiral shape so that it better conforms to the shape of the scala tympani. See, e.g., U.S. Pat. No. 4,819,647. The '647 U.S. patent is incorporated herein by reference. Unfortunately, while the electrode array with spiral-shaped carrier shown in the '647 patent represents a significant advance in the art, there exists lack of sufficient shape memory associated with the carrier to allow it to return to its original curvature (once having been straightened for initial insertion) with sufficient hugging force to allow it to wrap snugly against the modiolus of the cochlea.

It is also known in the art, as shown in applicant's prior patents, U.S. Pat. Nos. 5,545,219 and 5,645,585, to construct an electrode carrier from two initially straight members, a rodlike electrode carrier and a flexible rodlike positioning member. As shown in these patents, the two members extend in substantially parallel relation to and closely alongside each other, and remain connected to each other at least at their respective leading and trailing end regions. After implant, a pushing force is applied to the positioning member so that it is forced to assume an outwardly arched configuration relative to the electrode carrier, thereby forcing the electrode carrier into a close hugging engagement with the modiolus, thereby placing the electrode contacts of the electrodes in as close a juxtaposition to the cells of the spiral ganglion as possible. The '219 and '585 U.S. patents are also incorporated herein by reference. The '219 patent, in particular, provides in FIGS. 1–10 and accompanying text an excellent summary of prior art electrodes and the deficiencies associated therewith.

While the electrode array taught in the above-referenced '219 and '585 patents has the right idea, i.e., to force the electrode carrier into a close hugging engagement with the modiolus, it does so only by use of a system that makes manufacture of the lead more difficult and expensive, and only through application of an additional pushing force which is applied to an electrode structure after it is already fully inserted into the cochlea. Such additional pushing force may easily cause damage to the delicate scala tympani. Moreover, the entire electrode array may twist during the insertion process, or when the additional pushing force is applied, thereby causing the electrode contacts to twist and/or be forced away from the modiolus, rather than in a hugging relationship therewith.

Applicants prior U.S. patent applications—e.g., Ser. No. 09/140,033, filed Aug. 26, 1998, and Ser. No. 09/140,035, filed Aug. 26. 1998, both of which are incorporated herein by reference—disclose various other types of modiolar-hugging electrodes and systems that may be used to achieve the desired goal of placing the electrode contacts near the modiolar wall.

Thus, while it is known that an enhanced performance of a cochlear implant may be achieved by proper placement of the electrode contacts close to the modiolar wall of the cochlea, two main problems have faced designers in attempting to achieve this goal. First, it is extremely difficult to assemble electrode contacts on the medial side of the an electrode array, facing the modiolus of the cochlea. Second, heretofore there has either been the need for application of an external (and perhaps unsafe) force, or a lack of sufficient shape memory, to allow the electrode (after initial straightening to facilitate insertion) to assume or return to the desired curvature needed to place the electrodes against the modiolar wall so that the curvature wraps snugly around the modiolus of the cochlea. As a result, the electrode contacts of the prior art electrodes generally remain positioned too far way from the modiolar wall.

Many cochlear electrode arrays of the prior art are made for insertion into a left cochlea, or a right cochlea, depending upon the orientation of the electrode contacts one to another. It would be desirable for a universal electrode array to be made that could be used in either cochlea, left or right, without concern for whether the electrodes were orientated in a right or left side orientation.

It is thus evident that improvements are still needed in cochlear electrodes, particularly to facilitate assembling an electrode so that the electrode contacts are on the medial side of the electrode array, and to better assure that the electrode assumes a close hugging relationship with the modiolus once implantation of the electrode has occurred.

SUMMARY OF THE INVENTION

The present invention addresses the above and other needs by providing a universal electrode array system, adapted for insertion into either a left or right cochlea, which provides improved stability of electrode contact direction. Such universal electrode array system includes a cochlear electrode array, e.g., of the type disclosed in Applicant's copending patent application Ser. No. 09/247,734, combined with an electrode positioner, e.g., of the type disclosed in Applicant's copending patent application Ser. No. 09/216,063, now U.S. Pat. No. 6,078,841 both of which applications have been and are incorporated herein by reference. Advantageously, in accordance with the present invention, such electrode array and positioner are combined as a single system, with a distal tip of the positioner being joined to the electrode array near the distal tip of the electrode array. Thus, as one of the elements is inserted into the scala tympani duct of the cochlea, the other element is carried with it, allowing both elements of the system to be jointly inserted into the cochlea during a single implant operation. Such insertion may be facilitated, e.g., using an easy-to-use insertion tool of the type previously used to insert the positioner.

In accordance with one aspect of the present invention, the electrode array component of the electrode system advantageously has all of the electrode contacts spaced apart along one edge or side of the array, termed the "medial side". Moreover, the structure of the electrode array facilitates bending of the array with the electrode contacts on the inside of the bend, yet deters flexing or twisting of the array that would tend to position or point the electrode contacts away from the inside of the bend. Hence, when inserted into the scala tympani duct of a cochlea, all of the electrode contacts on the medial side of the array generally face the modiolus wall of the cochlea.

In accordance with another aspect of the invention, small non-conductive bumps or humps may be formed in the electrode array between the electrode contact areas on the medial side of the array. These small bumps may be made, e.g., from a soft silicone rubber, or equivalent substance. When inserted into the cochlea, the small bumps serve as non-irritating stand-offs, or spacers, that keep the electrode contacts near the modiolus wall, but prevent the electrode contacts from actually touching the modiolus wall. These bumps may also serve as dielectric insulators that help steer the stimulating electrical current in the desired direction, towards the modiolus wall, as taught, e.g., in copending U.S. Pat. application Ser. No. 09/137,033, filed Aug. 20, 1998, assigned to the same assignee as the present application, and incorporated herein by reference.

In accordance with yet another aspect of the invention, a distal tip of the positioner, which forms one component of the electrode system, is attached at one point to the electrode array, another component of the electrode system, near, but not at, the distal tip of the electrode array. This allows the positioner, when inserted into the cochlea, to reside behind the electrode array, filling the space behind the electrode array, and forcing the electrode contacts of the electrode array to be positioned against or near the modiolus wall. Further, because the positioner is attached to the electrode array near the distal tip of the electrode array, the electrode array and positioner may be inserted into the cochlea at the same time, using, e.g, the same insertion techniques previously used to insert the positioner. In general, such insertion techniques rely upon the use of a stylet wire threaded into a lumen or channel that passes longitudinally through the positioner. The stylet wire, with the positioner component of the system threaded thereon, may be gently guided and pushed, as required, in order to steer and slide the positioner, and the electrode array which is connected to it, into the scala tympani (or other duct) of the cochlea to the desired depth. Advantageously, because the distal tip of the electrode array protrudes distally a short distance beyond the point where the distal tip of the positioner joins the electrode array, the protruding distal tip of the electrode array may function as a soft bumper as the electrode assembly is slid into and through the bends of the spiraling cochlea, thereby minimizing the risk of any serious damage or trauma to the cochlea or the patient as the implant operation is carried out.

In accordance with still a further aspect of the invention, both components of the electrode system of the present invention—the universal electrode array and the positioner—can be manufactured using easy, low cost technology; and once made can be easily inserted, removed and reinserted, if required, into the cochlea or other curved body cavity.

Advantageously, the cochlear electrode system of the present invention achieves the following goals: (1) it assures that the electrode contacts of the electrode array are optimally positioned facing the medial direction, e.g., facing the modiolar wall in a cochlea of any size or any side (left or right) of the body; (2) it assures the electrode contacts, or alternatively the non-conductive humps or bumps (if used) between the electrode contacts, are positioned against the modiolar wall; (3) it may be manufactured using easy, low cost technology; and (4) it may be easily inserted into the cochlea, and removed and reinserted, if required.

It is a feature of the present invention to provide a space-filling electrode system for use in a cochlea that positions the electrode contacts of an electrode array near the modiolar wall of the cochlea and that may readily be inserted into the cochlea with minimal effort and without serious risk of injury or trauma to the cochlea or the patient.

BRIEF DESCRIPTION OF THE DRAWINGS

The above and other features and advantages of the present invention will be more apparent from the following more particular description thereof, presented in conjunction with the following drawings wherein:

FIG. 3 illustrates a side profile view of a positioner, and further illustrates a desired curve of the positioner at its distal tip;

FIG. 3A is a sectional view taken along the lines 3A—3A of the positioner of FIG. 3;

FIG. 3B is a sectional view taken along the line 3B—3B or 3C—3C of the positioner of FIG. 3;

FIG. 4 is a proximal end view of the positioner of FIG. 3;

FIG. 12 illustrates the electrode system of the present invention which comprises an electrode array joined to a positioner at or near the distal tip of the array and positioner;

FIG. 12A is a section view of the positioner taken along the line 12A—12A of FIG. 12;

FIG. 12B is a sectional view of the electrode array taken along the line 12B—12B of FIG. 12;

FIG. 12C is a detailed view of the electrode system of FIG. 12 at the point where the distal tip of the positioner is joined to the electrode array near the distal tip of the electrode array;

Corresponding reference characters indicate corresponding components throughout the several views of the drawings.

DETAILED DESCRIPTION OF THE INVENTION

Figure 1:
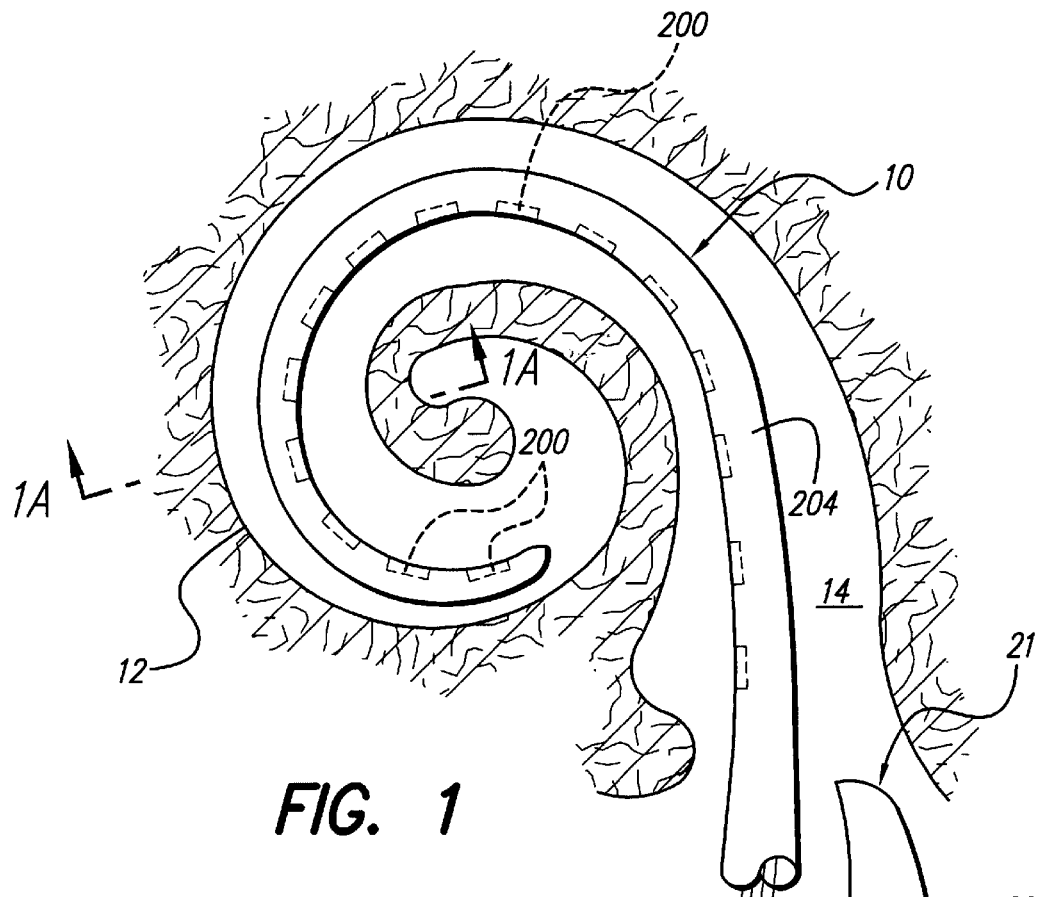
FIG. 1 is a schematic representation of the scala tympani duct of the cochlea showing the inter-relationship of the two components of the electrode system of the present invention when the two components are used separately, and illustrates the electrode array first inserted into the cochlea and shows the positioner inserted second into the cochlea.

The following description is of the best mode presently contemplated for carrying out the invention. This description is not to be taken in a limiting sense, but is made merely for the purpose of describing the general principles of the invention. The scope of the invention should be determined with reference to the claims.

The invention described herein teaches a particular type of implantable electrode array system intended for use with a cochlear stimulation system. The electrode system of the present invention is designed to be inserted deep into the cochlea of the user of the cochlear stimulation system.

The electrode system of the present invention is made from two main components: (1) an electrode array having electrode contacts, and (2) a positioner joined at its distal tip to the electrode array near its distal tip. Because each of the components of the electrode system described herein may be made separately, and joined together later, and each component after being joined to the other continues to serve its separate function, it will first be instructive to describe each component separately, and the function served by each component, and then describe how the two components are joined together and inserted into the cochlea.

Accordingly, the description presented below in conjunction with FIG. 1 through FIG. 5B relates primarily to the positioner component of the invention, and provides an overview or summary of the positioner described in Applicant's copending patent application, "Flexible Positioner For Use With Implantable Cochlear Electrode", Ser. No. 09/216,063, filed Dec. 18, 1998, now U.S. Pat. No. 6,078,841 previously incorporated herein by reference. In a similar manner, the description presented below in conjunction with FIG. 6 through FIG. 11 provides an overview or summary of a preferred universal electrode array described in Applicant's copending patent application, "Cochlear Electrode Array with Electrode Contacts on Medial Side", Ser. No. 09/247,734, filed Feb. 9, 1999, also previously incorporated herein by reference. Following the description of each of these main components of the invention—the positioner and the electrode array—the electrode system of the present invention is described in conjunction with FIG. 12 through FIG. 15. This description includes a description of a preferred manner of attaching the positioner to the electrode array, and a preferred manner for inserting the electrode system into the cochlea. It is to be emphasized that the description of the components—the positioner and the electrode array—provided in FIGS. 1–11 is intended as a summary or overview, and that additional details associated with each component may be found in the referenced patent applications.

The electrode system of the present invention may be best used with an implantable multichannel pulse generator, e.g., an implantable cochlear stimulator (ICS) of the type disclosed in U.S. Pat. No. 5,603,726, incorporated herein by reference, or other suitable stimulator. It is to be understood, however, that although a cochlear electrode array is hereafter described, having dimensions suitable for insertion into the cochlea, the principles of the invention may be applied to other types of implantable leads for applications other than cochlear stimulation.

Unless noted otherwise, the materials from which the electrode system of the invention is made, and the manner of making the electrode array, may be conventional, as are known in the art.

Turning first, then, to a description of the positioner, it is noted that the function of the positioner is to fill the space behind the electrode so as to position the electrode-contact side of the electrode array against the modiolar wall of the cochlea. A preferred positioner is shown and described below in connection with FIGS. 1 through 5B. However, it is to be noted that the positioner that forms part of the electrode system of the present invention is not limited to the preferred positioner shown in these figures. Rather, any positioner that comprises an elongate flexible element that effectively fills the space behind the electrode array so as to force or position the electrode array near the modiolar wall of the cochlea could be used with the invention.

Figure 1A:
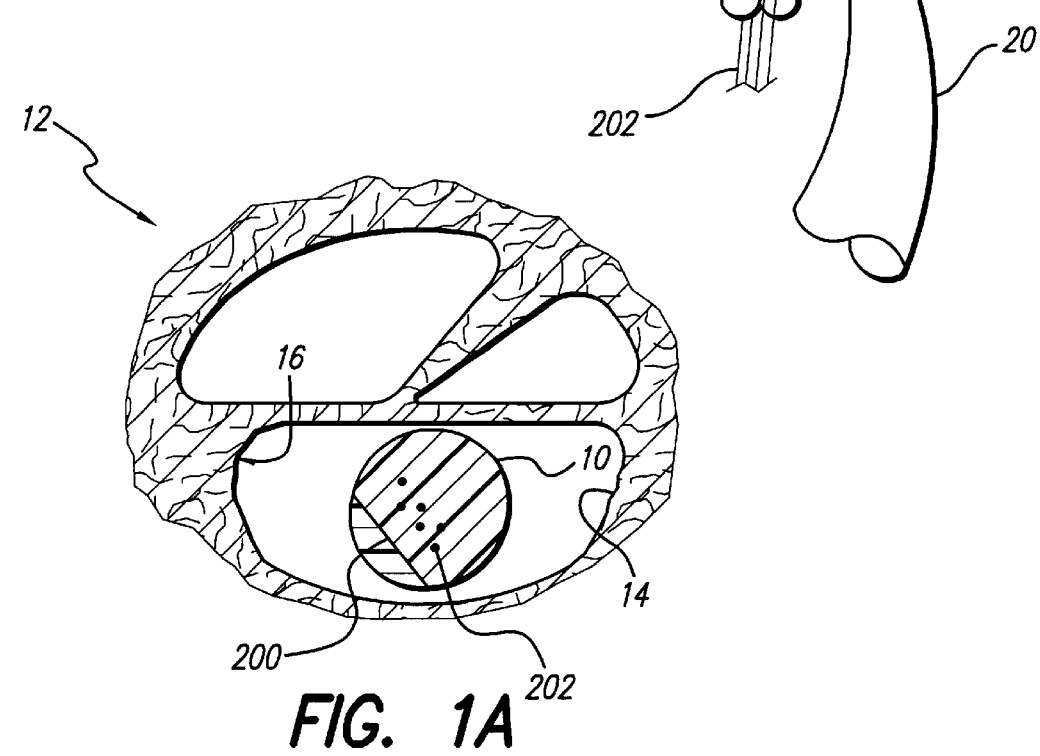
FIG. 1A is a sectional view taken along the line 1A—1A of FIG. 1.

In general, as illustrated in FIGS. 1 and 1A (which show a typical electrode array 10 inserted into the scala tympani duct 14 of a cochlea 12), an electrode array 10 includes a plurality of spaced-apart electrodes 200, formed within a flexible carrier 204. Each of the electrodes is connected to at least one wire 202 which is embedded within the carrier 204. A proximal end of the these wires 202 (not shown) allows selective electrical connection to be made with each electrode 200 through use of a tissue stimulator, e.g., a cochlear stimulator. The tissue stimulator, in turn, causes an electrical stimulus to appear between a selected pair of the electrodes 200, which stimulus is designed to provide direct electrical stimulation of the auditory nerve cells.

Also shown in FIG. 1 is the distal tip 21 of a flexible positioner 20 as the positioner is just starting to be inserted into the scala tympani duct 14 behind the electrode array 10. As will become more evident from the description that follows, the flexible positioner 20 is preferably made from a silicone polymer, in a pre-curved formed shape, with a width or cross-sectional area that is tapered, as required, to match the cross-sectional area or width of the scala tympani duct within the cochlea. The radius of curvature of the positioner is generally selected to be somewhat larger than the natural curvature of the scala tympani duct.

Heretofore, the electrode array 10 was inserted into the scala tympani 14 using any suitable technique, as is known in the art. If possible, during such insertion, the electrode contacts 200 of the electrode array 10 were oriented to face the modiolar wall 16 within the cochlea. Whether this was possible or not depended on the type of electrode array which was used. An electrode array of the type disclosed in Applicant's copending patent application, Ser. No. 09/140,034, now U.S. Pat. No. 6,078,841 previously referenced, is specifically designed so that all of the electrode contacts face the same direction. Such electrode array can be oriented so that all of the electrode contacts 200 face the modiolar wall, which is a preferred orientation.

When the electrode array is first inserted into the scala tympani 14, it typically tends to move towards the outer wall of the scala tympani, farthest away from the modiolar wall 16. That is, as seen in the schematic representation of FIG. 1, as well as the sectional view of FIG. 1A, when first inserted into the cochlea, in the absence of the positioner, the electrode array 10, including its electrode contacts 200, are not firmly held in position against the inner wall (modiolus) 16 of the cochlea. In order to force or hold the electrode array 10 up against the modiolus, the positioner 20 is also inserted into the cochlea, behind the electrode array 10, i.e., on the side of the electrode array 10 farthest from the modiolus, as seen in FIG. 1 (which shows the distal tip 21 of the positioner 20 just as it is first inserted behind the electrode array 10 within the cochlea).

As the positioner 20 is pushed deeper into the cochlea, it forces the electrode array 10 up against the modiolar wall 16, which action causes many of the electrode contacts 200 to be in direct contact (touching) with the modiolar wall. Moreover, as the positioner 20 is pushed still deeper into the cochlea, the movement of the positioner against the electrode array may tend to carry the electrode array 10 even deeper into the cochlea, e.g., causing the electrode array 10 to be inserted an additional ¼ to ½ turn deeper into the cochlea than when initially inserted.

Figure 2:
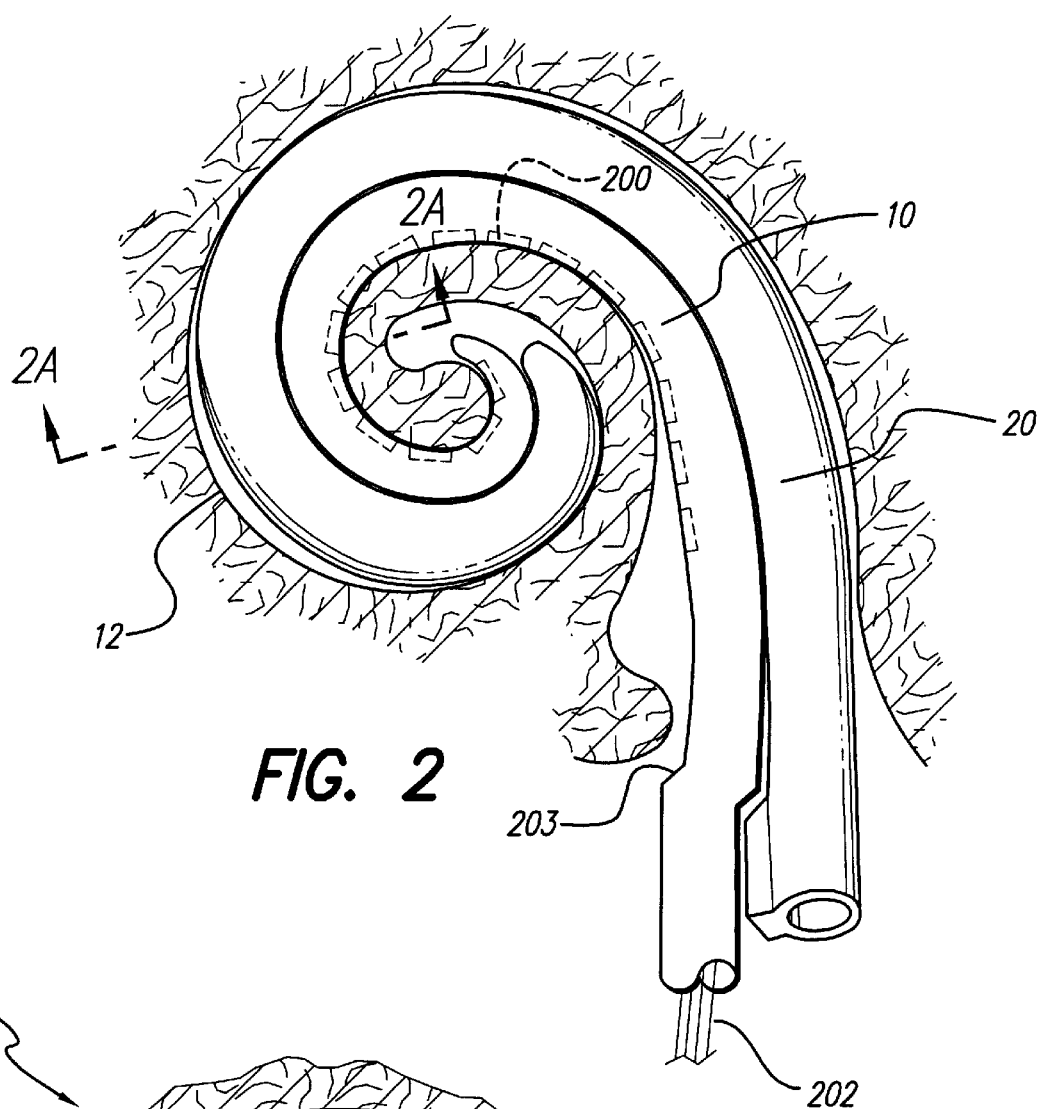
FIG. 2 is a schematic representation of the scala tympani duct of the cochlea as in FIG. 1, but showing the positioner fully inserted into the cochlea.
Figure 2A:
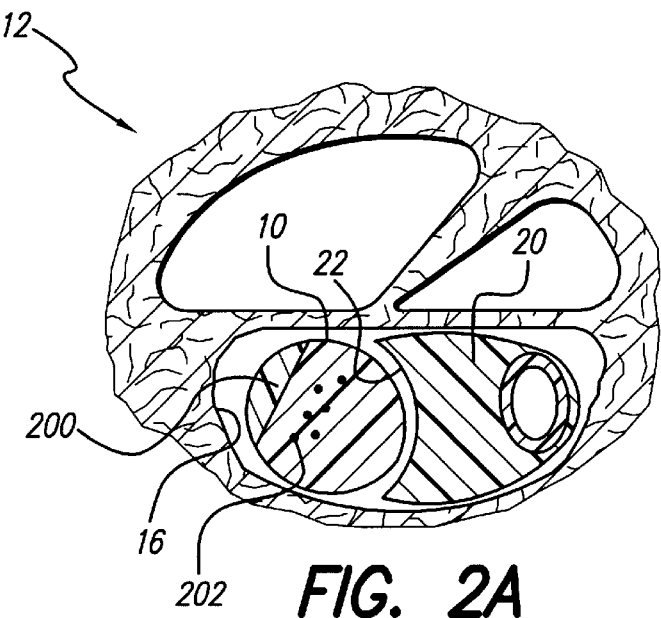
FIG. 2A is a sectional view of the cochlea taken along the line 2A—2A of FIG. 2.

A fully inserted electrode array 10 with positioner 20 is shown in FIGS. 2 and 2A. Note that the positioner 20 fills the available space within the scala tympani 14 and pushes the electrode array 10 up against the modiolar wall 16, as desired. A groove or channel 22 is formed along one side or edge of the positioner 20 to receive the electrode array 10 as the positioner is inserted into the scala tympani duct.

To aid in the insertion process, a suitable lubricant may be spread over the surface of the positioner 20, e.g., to form a coating thereon, prior to inserting it into the scala tympani duct behind the electrode array 10. Any suitable lubricant, e.g., a silicone oil lubricant, or a hydrophilic coating, may be used for this purpose. Such lubricants, or equivalent lubricants, have been used for years in order to help implant pacemaker leads. The use of equivalent lubricants, or other surface preparation techniques, is described, e.g., in U.S. Pat. No. 5,736,251, incorporated herein by reference.

As seen in FIG. 2, the electrode array 10 may have an offset 203 associated therewith. Heretofore, such offset 203 facilitated insertion of the electrode array and further functioned as a stop to prevent the electrode array 10 from being inserted too deep into the cochlea. Such offset, even if not used as a stop, can nonetheless function as a mark to aid the physician to know when the desired insertion depth has been achieved. One of the advantages of the electrode system of the present invention, as will be evident from the description of FIGS. 12–15 below, is that such offset 203 is no longer necessary in the electrode array, although such an offset 203 can be present if desired.

A preferred shape of the positioner 20 is illustrated in FIGS. 3, 3A, 3B, and 4. As seen best in FIG. 3, the positioner 20 assumes a general shallow hook shape. (Note, "shallow", in this context, refers to the fact that a distal tip or end portion 21 of the positioner bends only slightly more than 90 degrees, e.g., 120 degrees, from the longitudinal axis or center line of the positioner at the proximal end.) While a shallow hook shape is preferred for purposes of the positioner, it is to be emphasized that any curve shape may suffice, and indeed, no curve shape may also suffice when the body of the positioner is sufficiently flexible so that it can readily bend and conform to the contours of the spiral-shaped scala tympani. The curved shape helps prevent rotation of the positioner when inserted into the cochlea.

The positioner 20 preferably includes a channel or lumen 27 that passes longitudinally through the entire length of the body of the positioner. Typically, such channel 27 comprises the lumen of a silastic tube 23, which tube 23 forms the core of the positioner. That is, as explained in more detail below, during manufacture of the positioner 10, the silastic tube 23 has liquid silastic material molded and cured around it in order to form the positioner in the desired shape. In this manner, the silastic tube 23 becomes a tube molded into the positioner, or a "molded-in tube". At the distal tip 21, as seen best in FIG. 3, a plug 28 is placed to block the distal end of the channel 27. Such channel or lumen 27 is used to receive a guiding wire stylet, as explained below, when the electrode system is inserted into the cochlea.

A side channel or groove 22 is formed along one edge or side of the positioner body along its entire length, i.e., along the bottom side 26 (or inside-curve side) as the positioner is oriented in FIG. 3. Moreover, the positioner 20 is preferably tapered, as illustrated generally in the sectional views of FIGS. 3A, and 3B, which views are taken respectively at the lines 3A—3A (FIG. 3A), and 3B—3B or 3C—3C (FIG. 3B) of FIG. 3. The cross-sectional area of the positioner at the section lines 3A—3A is roughly W1×L4, whereas the cross-sectional area of the positioner at the section lines 3B—3B or 3C—3C is roughly L7×L8, where W1, L4, L7 and L8 are representative dimensions, having typical values as indicated below.

A guiding tab 25 may also be formed at the proximal end of the positioner 20 on the bottom side 26 (the same side as the groove or channel 22). Such tab 25 helps keep the positioner properly oriented without twisting as it is inserted into the cochlea.

Typical dimensions of a cochlear positioner made in accordance with this preferred embodiment of the invention are as identified in FIGS. 3, 3A, 3B and 4 and as presented below. Such dimensions and shape are not intended to be limiting, but are presented merely to show a preferred and best mode for the positioner. Other dimensions and shapes could, of course, be used so long as the positioner is able to fulfill its basic function of pushing or positioning the electrode array against the modiolar wall of the scala tympani duct.

Referring, then, to the preferred embodiment of the positioner shown in FIGS. 3, 3A, 3B and 4, the length L1, of the tab 25 is typically 0.069±0.008 inches. The length L2, of the straight portion of the positioner is about 0.61 inches. The depth L3 that the plug 28 is inserted into the distal tip of the channel 27 is about 0.04 inches. The height L4 of the positioner at is proximal end, from the edge of the tab 25 to the top side of the positioner, is about 0.051 inches. The length L5 from the top side of the positioner, at its proximal end, to the bottom edge of the tab 25 is about 0.091 inches. The width W1, of the positioner at its proximal end is about 0.059 or 0.060 inches, making the distance L6 from the center of the tube 23 to the side of the positioner, at its distal end, about 0.03 inches. The distance L9 from the center of the molded-in tube 23 to the top of the positioner, at its distal end, is about 0.012–0.013 inches. The width W2, of the tab 25 is approximately 0.039 inches.

The overall dimensions (cross-sectional shape) of the positioner linearly taper from its proximal end to approximately the end of the straight section L2, e.g., at about the point where the cross-sectional line 3B—3B is placed. At the section line B—B, the dimensions are as shown in FIG. 3B, with the height L7 and the width L8 of the positioner being about 0.037 and 0.039 inches respectively.

The molded-in silastic tube 23 has an inner diameter (I.D.) of about 0.012 inches and an outer diameter (O.D.) of 0.025 inches, making the thickness of the tube walls about 0.006–0.007 inches. The bottom of the grove or channel 22 is formed so as to be near the edge of the tube 23 at the proximal end of the positioner and at the edge of the tube 23 at the distal end of the positioner. The radius R2 associated with the formation of the curved channeling groove 22 is typically about 0.016 inches. This radius R2 remains more or less the same along the entire length of the positioner.

The shallow hook at the distal end of the positioner is formed to have a radius of curvature R1 of about 0.117 to 0.197 inches. The curved or hooked distal tip 21 of the positioner curves at the radius R1 for an angle α2 of about 120 degrees beginning from the point where the straight section L2 ends and the curved or hooked section begins. Further, the distal tip 21 of the molded-in tube 23 is cut at an angle α1, where α1 is defined as shown in FIG. 3, before placement of the plug 28. In the preferred embodiment, the angle α1 is approximately 45 degrees.

Figure 5A:
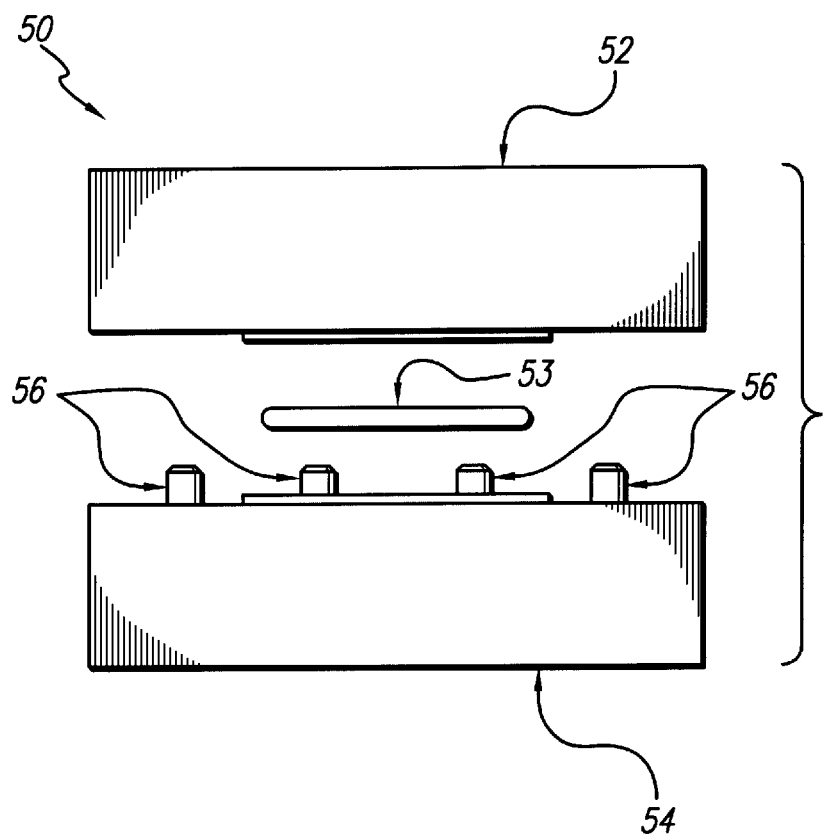
FIG. 5A illustrates a side view of a two-part mold that may be used to make the positioner of FIG. 3.

The positioner 20 is made using a mold 50, illustrated in FIG. 5A. Conventional molding techniques and principles are used to form the positioner 20, as are known to those of skill in the molding art. As seen in FIG. 5A, the mold has a top plate 52 and a bottom plate 54. As seen in both FIGS. 5A and 5B, the mold 50 basically includes removable stainless steel alignment pins 56 at key locations that align the top plate 52 with the bottom plate 54 when the two plates are attached together. Additionally, threaded holes 58 are provided to allow bolts or screws (not shown) to detachably secure and clamp the top plate 52 to the bottom plate 54 during the molding operation.

Figure 5B:
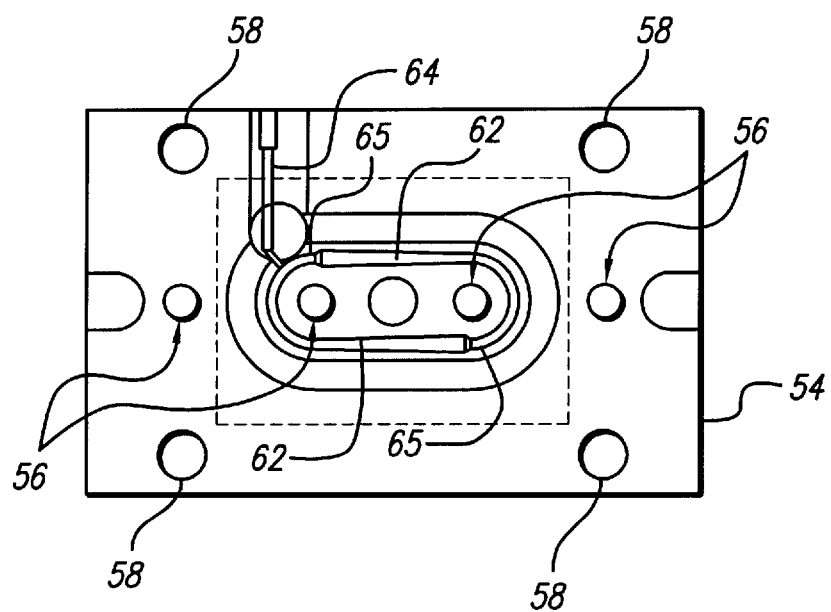
FIG. 5B illustrates a top view of the bottom part of the mold depicted in FIG. 5A.

Half channels 62 are formed in the top plate and bottom plate that define the desired shape of two positioners placed distal-tip-to-proximal-end. Only the bottom plate is shown in FIG. 5B, but the top plate has similar channels formed therein that are the mirror image of those shown in FIG. 5B. That is, two positioners 20 are molded simultaneously using the mold 50. The distal tip of each molded positioner is extended around its radius of curvature approximately another 600° in the mold. The desired shape of the positioner is as shown in FIGS. 3, 3A, 3B and 4. The excess distal tip portion, i.e, the extra 60° or so of curvature, is removed by trimming the distal tip after the positioner(s) has been formed and removed from the mold, as explained below. An injection port 64, which is in fluid communication with the half channels 62, is provided within the top and bottom plates to allow a liquid silastic mixture to be injected into the mold. A stop 65 provides a location for holding one end of a formed wire, placed inside of the proximal end of the lumen of the silastic tube during the molding operation, as also explained below. A mold insert 53, similar to an O-ring, is further placed between the top plate 52 and the bottom plate 54, surrounding the half channels 62, during the molding process.

The material from which the positioner and electrode array are made may be any suitable biocompatible material commonly used with implantable leads and other implantable components as is known in the art. A suitable material, for example, is a type of silicone polymer or rubber known as LSR-70 or LSR-25. The properties of LSR-70 and LSR-25 are well known in the art, and LSR-70 and LSR-25 may be obtained commercially from numerous sources. LSR-70 is formed into a desired shape by injecting or otherwise inserting it into a mold while in a liquid state and allowing it to cure in the mold at a specified temperature for a specified time period. For example, LSR-70 may cure at a temperature of 140 degrees C for about 15 minutes. LSR-25 may likewise be formed into a desired shape using a similar molding process, or it may be applied through a suitable applicator, e.g, a syringe, to a desired area and then formed into a desired shape. LSR-25 is essentially the same as LSR-70 except that when it cures it is significantly softer, i.e., more pliable.

Figure 6:
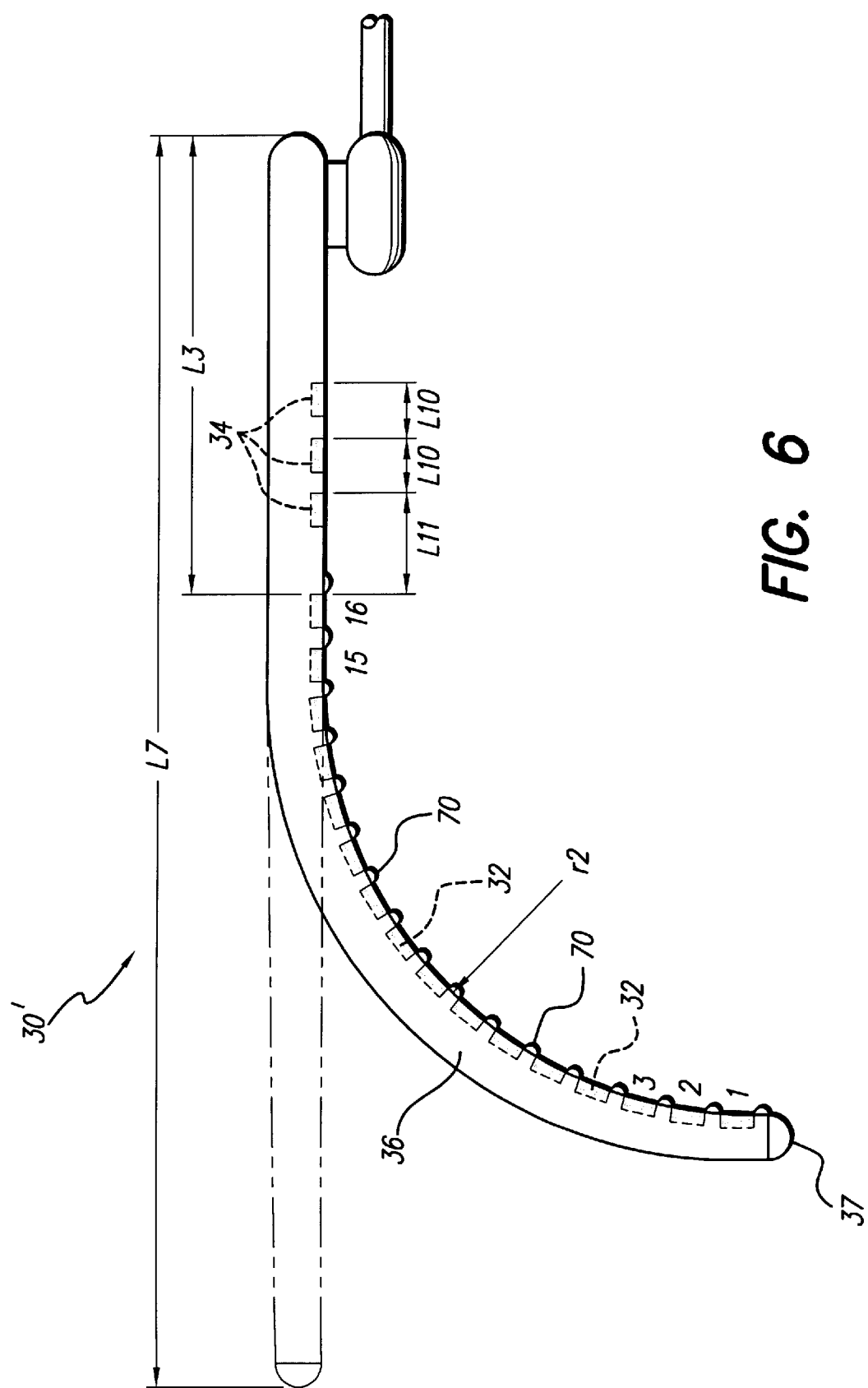
FIG. 6 shows one embodiment of an electrode array wherein bumps are formed in the space between each electrode contact.

Next, with reference to FIG. 6, one embodiment of a preferred electrode array 30' that may be used with the electrode system of the present invention is illustrated. It is to be emphasized that the embodiment of the electrode array described in FIG. 6, and in the related figures, represents only one type of electrode array that may be used with the invention. That is, any cochlear electrode array, whether it has all of its electrode contacts on the medial side of the electrode carrier or not, and whether it is fabricated as described in connection with FIGS. 7A through 11 or not, may be used with the electrode system of the invention. Other types of electrode arrays, for example, that may be used with the electrode system of the invention are disclosed in the various patents and patent applications that have been incorporated herein by reference. Thus, it is seen that in its broadest sense, the electrode system of the present invention is directed to an electrode array, of whatever type, that is jointed near its distal end to the distal end of a positioner. Thus, it is to be appreciated that the description of the electrode array component of the invention which follows is meant to be exemplary only, not limiting, of the type of electrode array that may be used in the electrode system.

Returning to FIG. 6, where a preferred electrode array is illustrated, it is seen that the distance from the proximal end of the electrode array 30' to the proximal edge of the most proximal electrode contact may be a distance L3. In the preferred embodiment, the distance L3 is about 10.5 mm.

The electrode array 30' shown in FIG. 6 includes electrode array contacts 32 equally-spaced along a medial side of a flexible carrier 36. The flexible carrier 36 is made from LSR-70 or LSR-25, or equivalent biocompatible silastic substances, and is molded around an assembly of electrode contacts 32 and interconnecting wires. A preferred approach for performing such molding, but not the only approach, is as described below in conjunction with FIGS. 7A–11 At least eight spaced-apart electrodes 32 are embedded within the flexible carrier 36.

The electrode array 30' shown in FIG. 6 has an overall length L7. Such length L7 is most easily measured when the array 30 is straightened, as shown by the phantom lines in FIG. 6. In the preferred embodiment, L7 has a value of approximately 25 mm. While the electrode array 30' could be formed to assume any desired shape, in the preferred embodiment it is formed to include a natural curve having a radius of curvature r2, with the electrode contacts 32 being positioned along the inside of the curve. The radius of curvature r2 may have a value of approximately 9.0 mm.

As further seen in FIG. 6, a soft tip 37 is formed at the very distal tip of the electrode array 30'. In one embodiment, this soft tip may have a length of approximately 0.3 mm. The soft tip 37 is preferably made from a material that is softer than the flexible carrier 36.

As additionally illustrated in FIG. 6, the electrode 30' has heretofore typically included reference marker contacts 34, spaced from the most proximal active electrode a distance L11, with a spacing between the reference marker electrodes of L10. In the preferred embodiment, the distance L11 is about 3.0 mm, and the distance L10 is about 1.0 mm. One of the advantages of using the electrode system described below in FIGS. 12–15 is that such reference electrode contacts 34 are generally not needed.

Figure 6A:
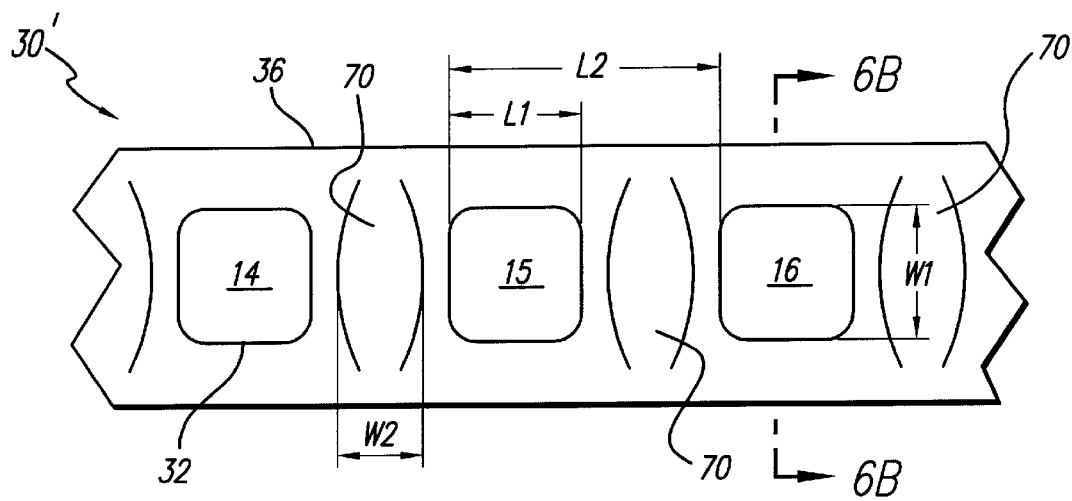
FIG. 6A shows a detail view of the electrode array contacts of the electrode array of FIG. 6.

Referring next to FIG. 6A, the preferred spacing between the individual electrode contacts 32 is depicted. Such spacing, as well as all the other dimensional detail presented herein, is exemplary of a cochlear electrode, and is not intended to be limiting. As seen in FIG. 6A, each exposed electrode contact surface area comprises a generally rectangular-shaped area having a length L1 and a width W1. Other shapes could also be used. In the preferred embodiment, the rectangular area is roughly a square, with L1 and W1 each having a value of approximately 0.4 mm±10%, thereby providing an exposed electrode surface area of approximately 0.16 mm$^2$. The spacing between corresponding points of adjacent electrode contact areas 32 is a distance L2. L2 has a nominal value of approximately 0.9 mm±0.1 mm.

Figure 6B:
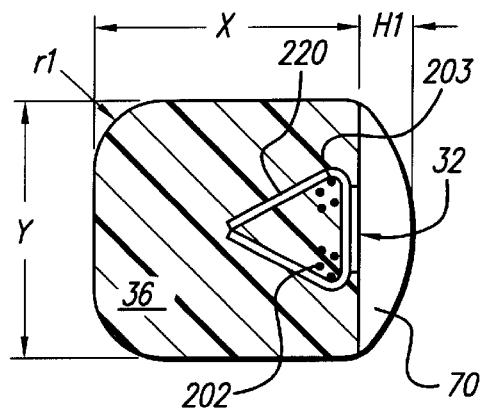
FIG. 6B is a sectional view of the electrode array of FIG. 6A taken along the line 6B—6B.

The electrode contact areas comprise an exposed surface of an electrode contact 32 that is formed from folded strips 210 and 220 of a biocompatible metal, such as platinum, as described more fully below in conjunction with FIGS. 7A–8D. Such electrode contacts are embedded within the molded carrier 36 as illustrated in the sectional view of FIG. 6B, which is taken along the lines 6B—6B of FIG. 6A. As seen in FIG. 6B, the carrier 36 is formed to have a cross-sectional area that is generally rectangular, having dimensions of X by Y mm, where the values of X and Y vary as a function of where along the length of the carrier the cross section is viewed. At electrode 16 (the most proximal active electrode of the electrode/array 30'), for example, X and Y are both about 0.8 mm. At electrode 1 (the most distal electrode of the electrode array), X and Y are both about 0.6 mm. Thus, it is seen that the carrier 36 is tapered along its length so that it has a smaller cross section at its distal tip than it does at its proximal end.

Still with reference to the cross-sectional view of the array shown in FIG. 6B, it is seen that the sectional shape has rounded corners on the side opposite the medial side. (As explained previously, the medial side is the side where the electrode contacts 32 are located.) The rounded corners have a radius of curvature r1 that is approximately 0.3 mm in the preferred embodiment.

The electrode contacts 32 may have a general cross sectional shape, as seen in FIG. 6B, and as will be more evident from the description below of FIGS. 7A–8D below, that resembles a triangle. The base of this triangular-shaped (or "Δ-shaped") electrode forms the exposed electrode contact area along the medial side of the electrode array, e.g., as seen in FIG. 6. The upward sloping legs 220 of this Δ-shaped electrode extend into the body of the carrier, e.g., as anchors, and thus become embedded (non-exposed) portions of the electrodes. It should be noted that while in the preferred embodiment the upward sloping legs 220 touch at their respective tips to form the Δ shape, such touching is not required; nor is the Δ shape required. What is important is that these legs 220 extend into the body of the carrier, in some fashion, so that the electrode is firmly anchored in its desired position along the length of the array. For example, in some embodiments, the legs 220 may be completely folded over so as to lie almost flat on top of the exposed surface area, as shown generally in parent application Ser. No. 09/140,034, filed Aug. 26, 1998, now U.S. Pat. No. 6,038,484. In other embodiments, the legs 220 may extend more or less straight into the body of the carrier, forming a generally block "U" cross-sectional shape.

Wire bundles 202 and 203 pass through the corners of the Δ-shaped (or other-shaped) electrodes and become embedded within the molded carrier 36 when formed. As explained in more detail below, at least one wire from at least one of these wire bundles makes electrical contact with each active electrode. The wires that do not make electrical contact with an electrode contact are nonetheless engaged by or supported by the embedded portion of the electrode as they pass through the Δ (or other) shape. Such engagement helps support and position the wire bundles prior to molding the carrier over them. Moreover, the location of the wire bundles immediately behind and along opposing edges of the exposed surface area of the electrodes helps add additional stiffness to the electrode array, once formed, in the lateral direction, as explained below, thereby making it more difficult to bend or twist the array in the lateral direction. In contrast, the array remains relatively easy to bend in the medial direction. As used herein, the medial direction is the direction of curvature defined by the radius r2 (FIG. 6).

As further seen in FIG. 6, the electrode array 30' may include a series of small non-conductive bumps, or humps 70, formed between the electrode contact areas 32. As seen best in FIG. 6B, these humps 70 have a height H1 of about 0.13 mm, and as seen best in FIG. 6A, have a width W2 of about 0.25 mm. As further seen best in FIG. 6, the humps 70 extend out from the medial surface of the electrode array. The humps 70 are made from a soft silicone rubber, or equivalent substance, such as LSR-25. When inserted into the cochlea, the small bumps 70 serve as non-irritating stand-offs, or spacers, that allow the electrode contacts 32 to be positioned near the modiolus wall, but prevent the electrode contacts 32 from actually touching the modiolus wall. The humps 70 further serve as dielectric insulators that help steer the stimulating electrical current, flowing to or from the electrode contacts, in the desired direction, from or towards the cells located in the modiolus wall, as taught, e.g., in the previously referenced copending U.S. patent application Ser. No. 09/137,033.

One of the advantages of using an electrode array 30' of the type illustrated in FIG. 6 is that the electrode array is easy and relatively inexpensive to manufacture. A preferred method of making the electrode array 30' is illustrated, for example, in FIGS. 7A through 11. It is to be emphasized that the method depicted in these figures of making the electrode array is not the only way an electrode array 30' could be made. However, it represents an easy and inexpensive (and thus a preferred) way to make the electrode array.

Most designs of electrodes and connectors are based on the principle of molding a contact or array of contacts, usually made from biocompatible metal, into a polymer carrier like silicone or polyurethane rubber. The electrode contacts are usually required to be located in a controlled position in reference to the surface of the carrier, with specified surface areas to be fully exposed to the stimulated or interconnection area. Disadvantageously, making such electrodes or connectors becomes extremely difficult, especially when the contacts are very small and/or a large number of contacts are required, e.g., as is the case with a cochlea electrode. One of the main problems encountered in the fabrication of such electrodes or connectors is to find a reliable method of holding the system of contacts in the desired and stable position during the process of welding the connecting wires and molding the polymer carrier. A further problem relates to maintaining a controlled surface of the contacts that are to remain exposed, i.e., to ensure that the contacts are not covered by the polymer when the carrier is molded.

The preferred methods of making the electrode array 30' described below in connection with FIGS. 7A through FIG. 11 are based on the principle of attaching (by the process of resistance welding) electrode contacts made from precious, biocompatible material (such as platinum or its alloys) to a foil carrier made from a non-toxic but chemically-active metal, such as iron (Fe). Resistance welding advantageously provides a secure attachment of the electrode material to the foil carrier without causing a deep fusion of the two materials being attached. The resulting shallow fusion contact, in turn, allows clean exposed electrode surface areas to be formed when the foil carrier is eventually chemically etched away, as explained below. Other types of attachment that result in shallow fusion of the electrode material and the foil carrier sheet material may also be used in lieu of resistance welding.

Attached to the metal carrier, the electrode contacts remain in a desired and stable position allowing easy connecting of the wiring system and subsequent molding of the polymer carrier. After completion of the molding process, the metal foil carrier is chemically etched away using a mixture of diluted acids, such as $HNO_3$ and HCl. The precious metal contacts and polymer are immune to the acid and remain in their intact, unaltered shape, and thereby provide the desired electrode array structure.

Figure 7A:
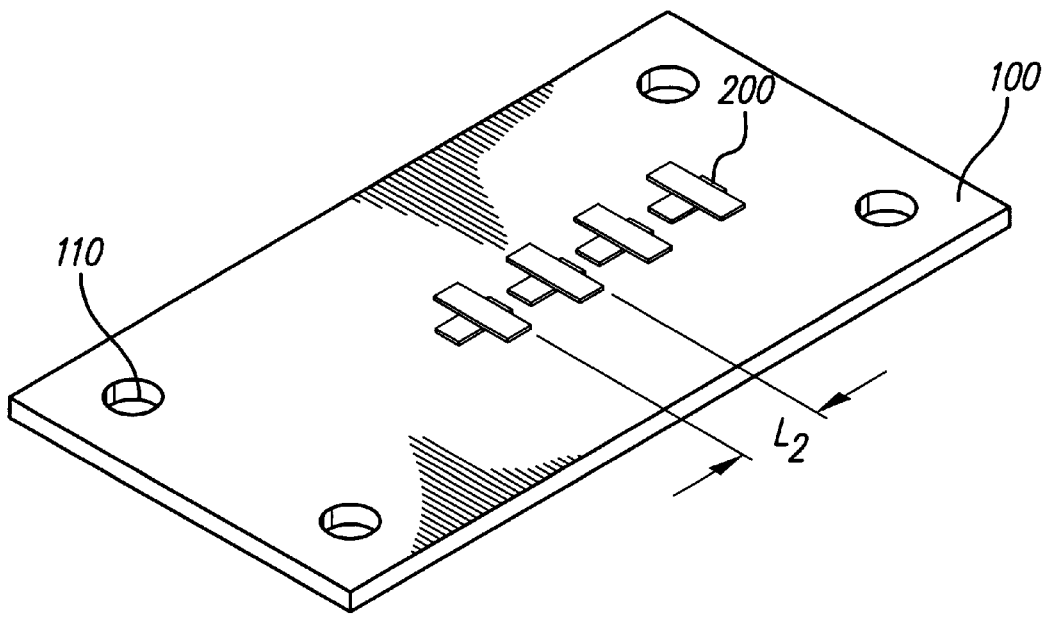
FIG. 7A depicts a preferred manner of making a multi-electrode contact array.
Figure 7B:
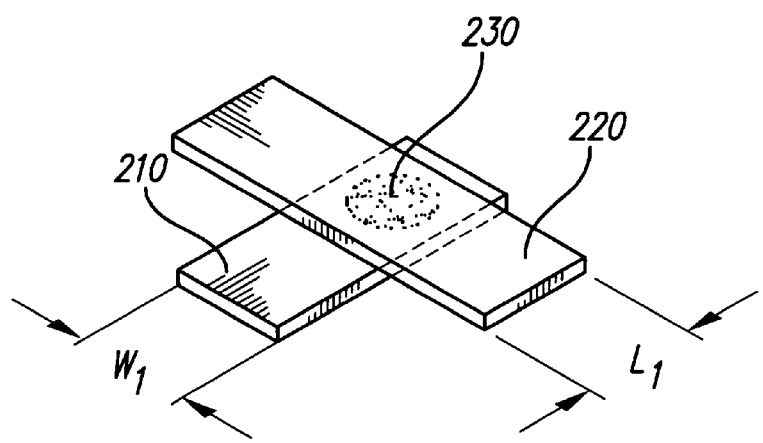
FIG. 7B shows an enlarged view the "T" strips used in making the electrode contacts of the array of FIG. 7A.

To illustrate, the method will be described relative to the fabrication of the electrode array 30' suitable for insertion into the cochlea. As a first step, an array of contacts 200 are resistance welded onto an iron carrier 100 so as to assume a desired in-line spaced-apart relationship, as shown in FIG. 7A. Each contact 200 consists of two pieces of platinum foil 210 and 220, connected together and joined to the carrier 100 by a shallow-fusion spot weld 230, as shown in FIG. 7B. The width of the strip 210 is approximately W1, and the width of the strip 220 is approximately L1. These strips are arranged to form a "T" shape, when viewed from a top view, with the strip 210 forming the leg of the "T", and with the strip 220 forming the cross bar of the "T". Moreover, the legs of each "T", are arranged in-line, with the proper spacing L2 therebetween, as shown in FIG. 7A.

As a second step, a wiring system is connected to each of the electrode contacts 200. This is accomplished as shown in FIGS. 8A, 8B, 8C and 8D. As seen in FIG. 8B, for example, an insulated wire 202', is laid on top of the electrode foil piece 220 (the cross bar of the "T"). The leg of the "T" of the foil piece 210 is then folded over to hold the end of the wire while the wire is welded in position (FIG. 8B). The welding process, preferably a resistance weld, burns away any insulation from the tip while making a secure mechanical and electrical connection between the wire and the electrode contact 200. The result is an electrode contact 200 having a wire 202' securely attached thereto (FIG. 8C). If other wires are present, e.g., going to more distal electrode contacts, then such wires may pass over the foil piece 210, lying more or less parallel to the wire 202' so as to form a bundle of wires 202. A similar bundle may be formed on the other side of the folded foil piece 210, thereby forming another wire bundle 203. The ends of the foil piece 220 are then folded upwards to form, in a preferred embodiment, a triangle, or Δ shape (as seen in a side view), as shown in FIG. 8D.

Figure 8A:
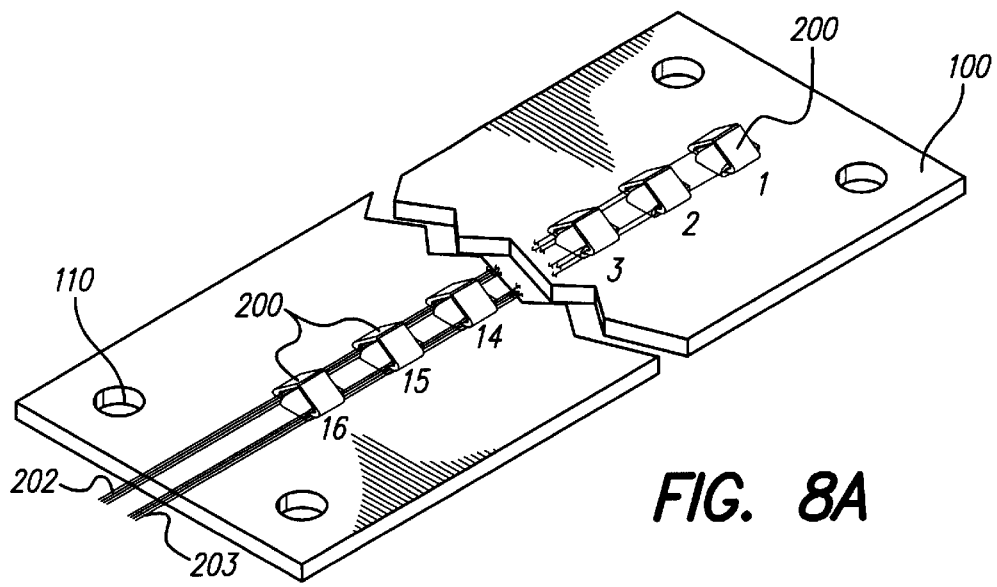
FIGS. 8A, 8B, 8C and 8D illustrate one manner in which wires are bonded and routed to each of the "T" strip electrode contacts of FIG. 7B during manufacture of the electrode array.
Figure 8B:
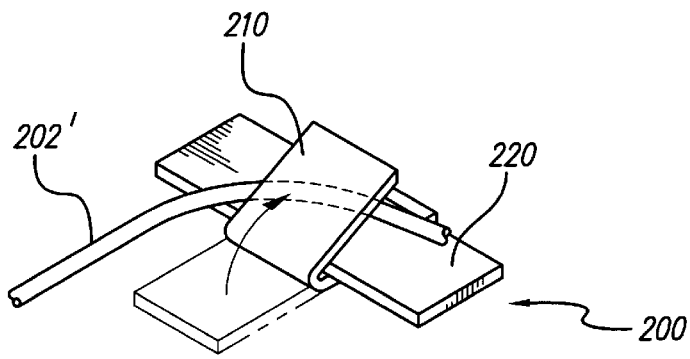
Figure 8C:
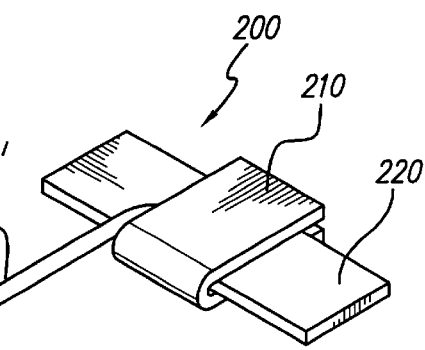
Figure 8D:
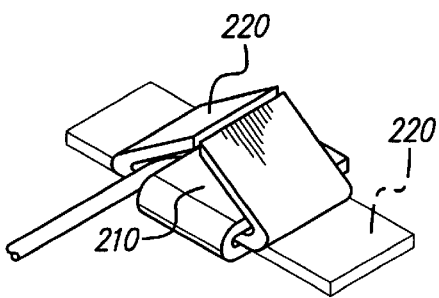

As seen in FIG. 8A, at least one wire from one of the bundles 202 or 203 is attached to the electrode contacts of the array 30'. (For simplicity, only six of the sixteen or nineteen electrode contacts used in the electrode array 30' are shown in FIG. 8A,) Typically, a wire from wire bundle 202 will connect to electrode contact 16, and a wire from bundle 203 will connect to electrode contact 15, and so on, with adjacent in-line electrode contacts being connected to wires from alternating wire bundles. At least two wires, one from each bundle 202 and 203 remain for connection to the most distal electrode contact 1. In this fashion, at least seventeen wires are used to make electrical connection with sixteen electrode contacts. In the preferred embodiment, for example, the wire bundle 202 may contain 9 wires, and the wire bundle 203 may contain 8 wires, for the sixteen-electrode array 30'.

Having a wire bundle on each lateral side of each electrode contact, e.g., as seen in the sectional view of FIG. 6B, and hence on each lateral side of the electrode array, helps add lateral stability to the array. This is true even when the wire "bundle" only contains one wire. Thus, an important feature associated with using two wire bundles in the manner described is that the wire bundles help add stiffness to the electrode array in the lateral direction, but do not materially affect the ability of the array to flex or bend in the medial direction.

Figure 9:
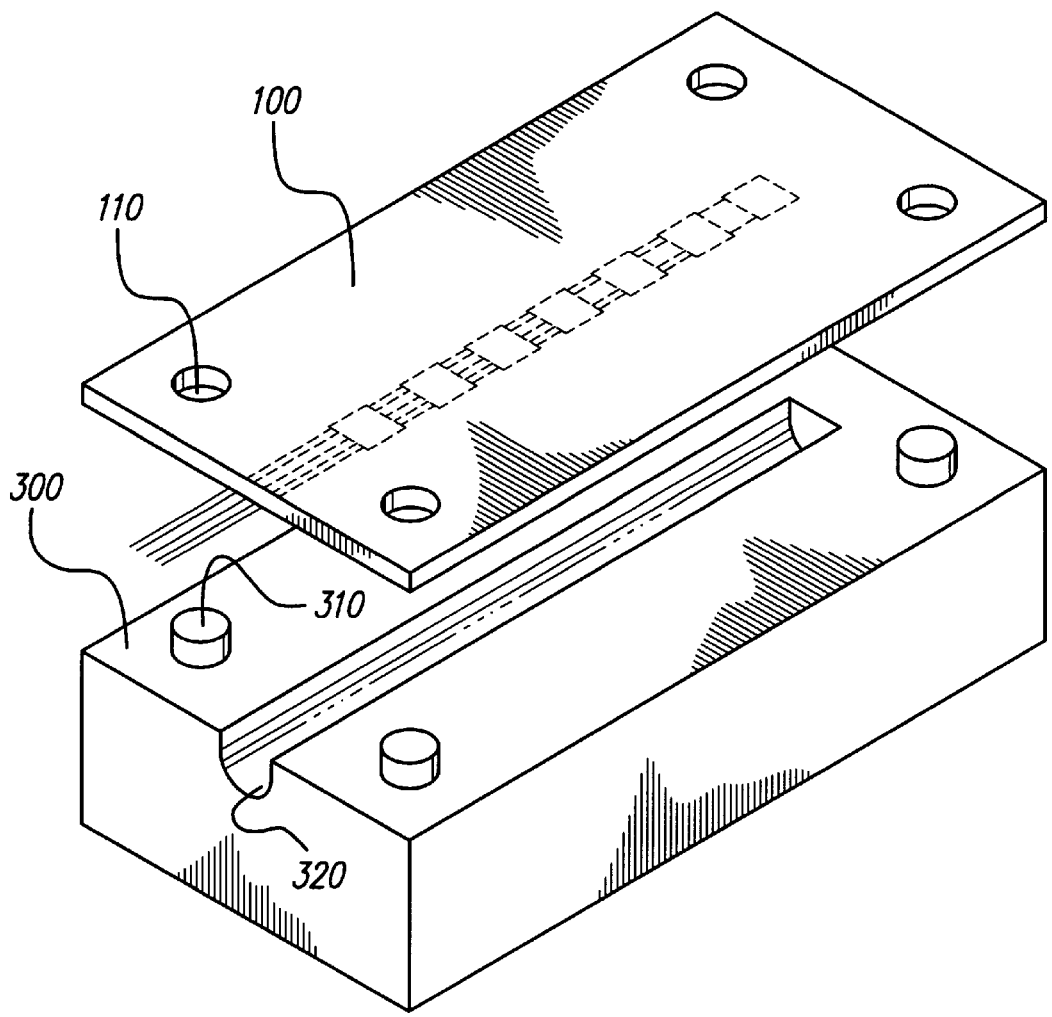
FIG. 9 depicts a molding die onto which the partially-formed electrode array of FIG. 7A, with wires attached to each of the electrodes as shown in FIGS. 8A–8D, may be mounted in order to form a straight polymer carrier for the electrode array.

Once the wire bundles 202 and 203 have been connected to all of the active electrodes 200, the foil carrier 100 may be placed on a molding die 300 as shown in FIG. 9. The die 300 has alignment pegs 310 adapted to align with corresponding alignment holes 110 in the foil carrier 100. The die 300 further has a cavity or channel 320 formed therein which the required amount of material, e.g., LSR-70, needed to form the polymer carrier 36 (FIG. 6) is injected. The LSR-70 is then cured in conventional manner. This cavity or channel 320 may be shaped or formed as desired. The mold depicted in FIG. 9 would form a straight carrier 36

Figure 10:
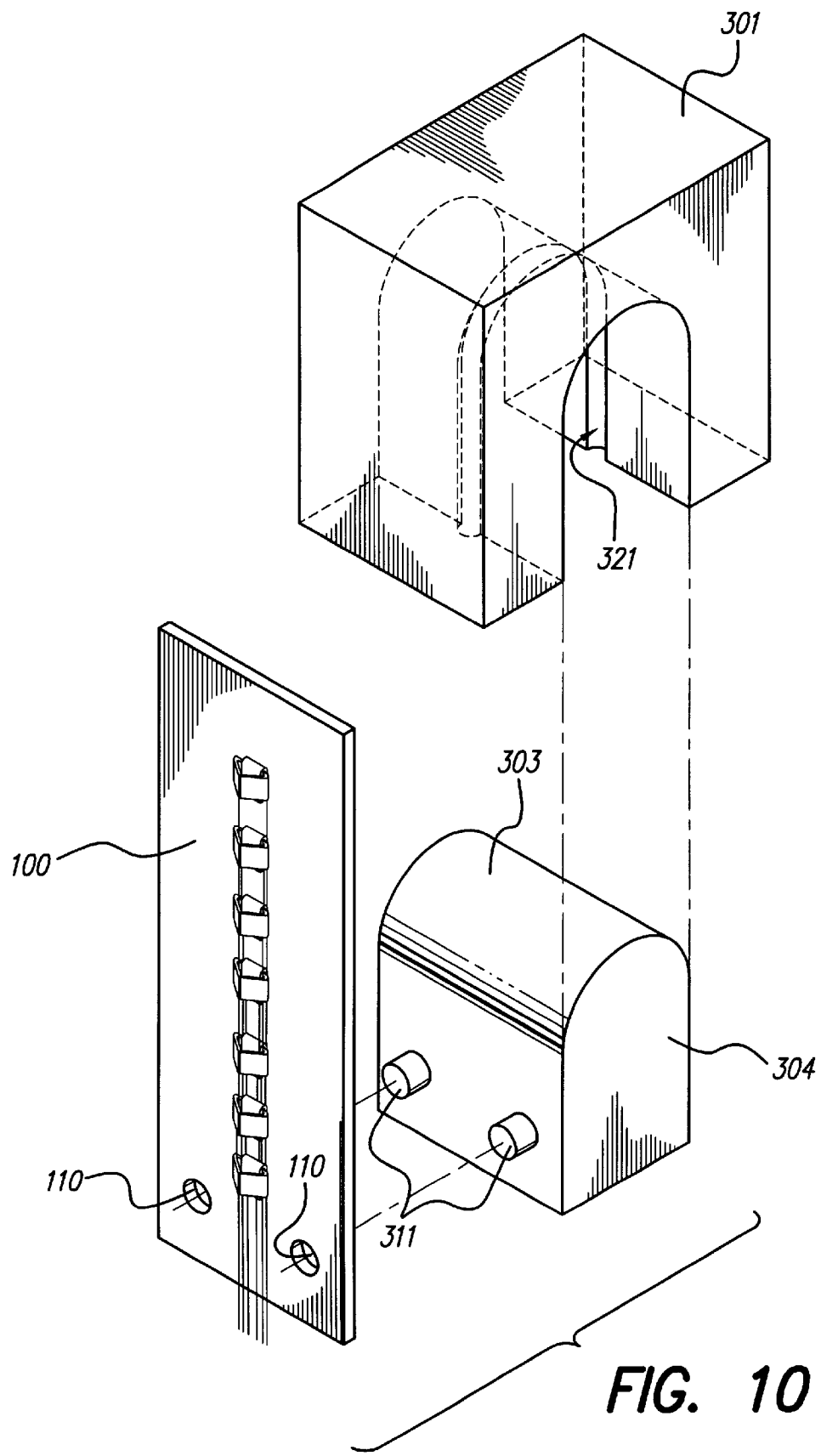
FIGS. 10 and 11 illustrate a perspective and side exploded view, respectively, of an alternative type of molding die onto which the partially-formed electrode array of FIG. 7A, with wires attached to each of the electrodes as shown in FIGS. 8A–8D, may be mounted in order to form a curved polymer carrier for the electrode array.
Figure 11:
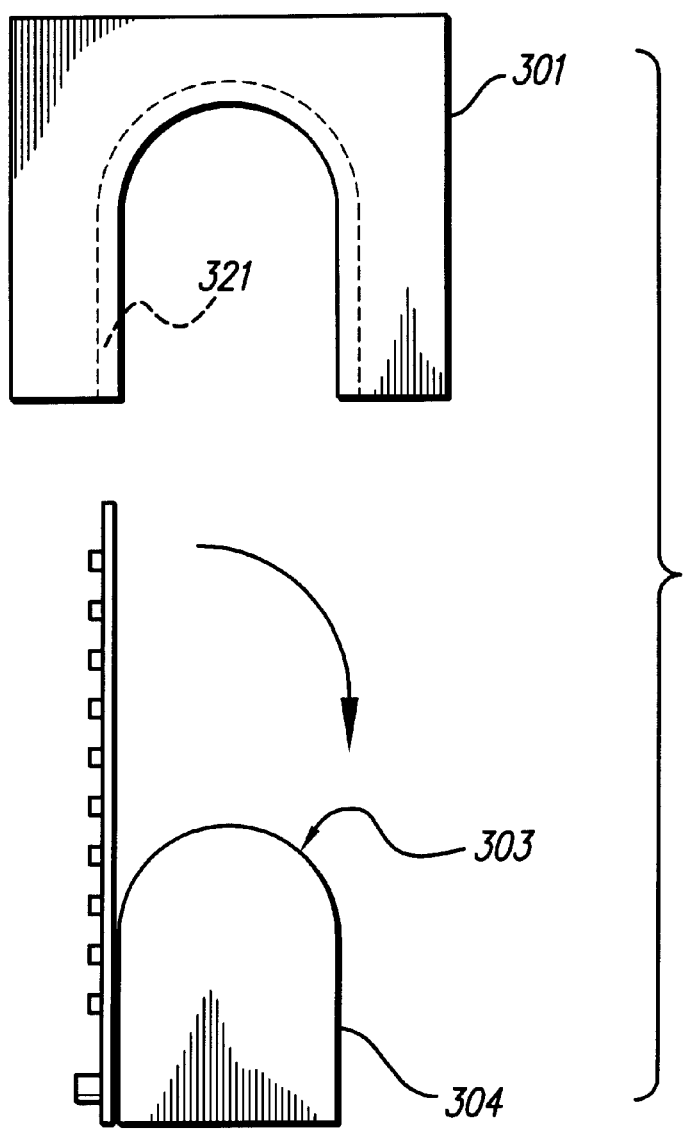

As an alternative to the flat-surface die 300 shown in FIG. 9, a curved die 301 is preferably used as shown in FIGS. 10 and 11. Such die 301 includes a curved surface 303 on a holding block 304 on which the foil carrier 100 may be placed. The block 304 has alignment pegs 311 adapted to align with corresponding alignment holes 110 in the foil carrier 100. The foil carrier 100 is placed on the block 304 and bent over the curved surface 303. The die 301 is then placed over the block 304, with the foil carrier 100 sandwiched therebetween. A channel or cavity 321 is formed in the die 301 having the desired shape and characteristics of the carrier that is to be formed through the molding process. The required amount of material to form the polymer carrier 36, e.g., LSR-70, is then injected into the channel and allowed to cure. By placing the foil carrier assembly 100 in the curved die of FIGS. 10 and 11 (note that FIG. 10 comprises a perspective view of the die 301 and block 304, and FIG. 11 comprises a side or profile view of the die 301 and block 304), the array can be molded or formed to assume the desired curved shape. Such curved shape is preferred to achieve directional stability of the array during insertion.

Thus, it is seen that through proper use of the die 300 or 301/304, or other dies, the electrode array may be formed to assume a natural curved shape, a slightly curved shape, or to be straight.

After the material used to form the carrier (e.g., LSR-70) cures, the foil carrier with the electrode array assembly (which is now molded inside of the polymer) is removed from the channel of the die 300 or 301/304 and placed in a mixture of diluted acids. The mixture of diluted acids dissolves the foil carrier 100, thereby exposing a clean surface of the electrode contacts 200. After washing to remove any residue of acids and iron salts, the main electrode array structure is completed.

An important feature of the electrode array 30' is that all of the active electrode contacts of the array are positioned along one side, e.g., the medial side (the inside of the curve or bend), of the array. Thus, when inserted into the curved or spiraling cochlea, which may advantageously be either a left or right cochlea, wherein the cells to be stimulated are located within the center modiolus wall, the electrode contacts are positioned proximate the modiolus wall, where they are closest to the cells to be stimulated. Hence, the electrode array of the present invention facilitates stimulation of the desired cells at lower power levels than would otherwise be needed if the electrode contacts were not proximate the modiolus wall.

Another feature of the electrode array 30' is that the electrode contacts have, in the preferred embodiment, a relatively large exposed electrode surface area that is generally planar or flat having a desired geometric shape, e.g., rectangular, semicircular, or oval. However, it is to be understood that the principles of the invention may also be practiced with electrodes that have exposed surface areas that are not flat, e.g., dimpled, or corrugated, or pitted, and that may have an exposed surface area that has irregular geometric shapes.

As has been indicated, the electrode array 30' is particularly adapted to bend or flex in one direction, thereby making it suitable for insertion into a curved body cavity, such as the cochlea. That is, the structure of the electrode array 30, as seen best in the sectional view of FIG. 6B, bends or flexes more easily in the medial direction than in the lateral direction. That is, the electrode array 30', with its slight curved shaped, when inserted into the cochlea, is able to bend, as required, to follow the scala tympani duct of the cochlea (whether the right or left cochlea) as it is inserted deeper and deeper into such duct. As it does so, the electrode contacts 32 remain closest to and facing the modiolus wall, as desired. As the electrode array is inserted deeper into the cochlea, the electrode array does not easily twist, or bend laterally, which twisting or bending could move the electrode contacts away from the modiolus wall. This is because the electrode array is inherently stiffer in the lateral direction than in the medial direction due primarily to the presence of the wire bundles and folded/bent electrode contacts which provide an added degree of stiffness in the lateral direction.

An electrode system 250 made in accordance with the present invention combines the positioner 20 with the electrode array 30' as depicted in FIG. 12. More particularly, the distal tip 21 of the positioner 20 is glued, or otherwise affixed to, the electrode array 30' near the distal tip of the array 30'. Except for this one connection or attachment point, the electrode array 30', and the positioner 20, remain the same as shown previously, and as depicted in the respective cross-sectional views of FIGS. 12A (showing a cross-sectional view of the positioner) and FIG. 12B (showing a cross-sectional view of the electrode array 30').

The preferred location for affixing the distal tip 21 of the positioner 20 to the electrode array 30' is near the third or forth most-distal electrodes 32 of the array (corresponding to electrodes 3 and 4 of the array). For a cochlear electrode, the attachment point of the distal tip 21 of the positioner is thus about three to four millimeters from the distal tip of the electrode array 30'.

One way to attach the distal tip 21 of the positioner 20 to the electrode array 30' is to glue the tip 21 to the body of the electrode array using a suitable silicone adhesive 260, as seen in FIG. 12C (which shows an enlarged view of the connection point). For example, a silicone adhesive known as Silastic "A", commercially available from Dow Corning Chemical Company, may be used for this purpose.

In connecting the distal tip 21 of the positioner 20 to the body of the electrode array 30', a suitable adhesive 260 is applied to the surface of the electrode array and the distal tip of the positioner, as required, to fill and smooth the space between the distal tip 21 and the surface of the electrode body. Typically, the adhesive, when applied in this manner, will have a length L12, of from 0.5 to 1.0 mm, as illustrated in FIG. 12C.

In order to strengthen the attachment of the distal tip 21 to the electrode array 30', particularly when under a compressive force, i.e., when pushing on the positioner from a proximal to a distal direction (as would occur when pushing the electrode assembly into the cochlea), a pin 262, with a head 263, is inserted at the end of the channel 27 that passes longitudinally through the positioner 20. The pin 262 extends into the adhesive, and provides additional structure to which the adhesive may bond in order to form a stronger bond. In particular, the pin structure illustrated in FIG. 12C makes the joint formed between the distal tip of the positioner and the electrode array 30' very secure when pushing on the positioner (applying a compressive force), as occurs when inserting the electrode system 250 into the cochlea. On the other hand, should the need arise to remove the positioner, the adhesive bond formed between the distal tip of the positioner and the electrode array 30' may generally be broken, or pulled apart, by pulling on the positioner (applying a tension force).

Figure 13:
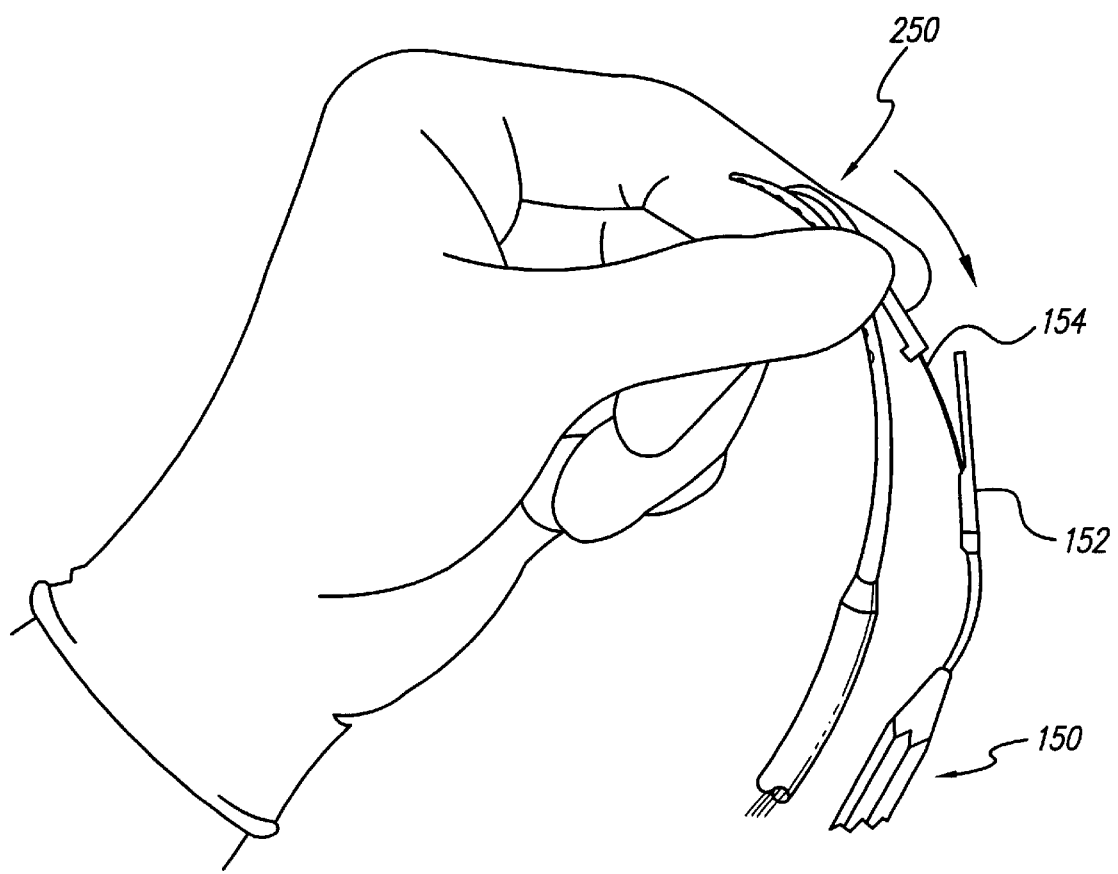
FIG. 13 illustrates a preferred technique for loading the electrode system of FIG. 12 into an insertion tool prior to inserting the system into a cochlea.
Figure 14:
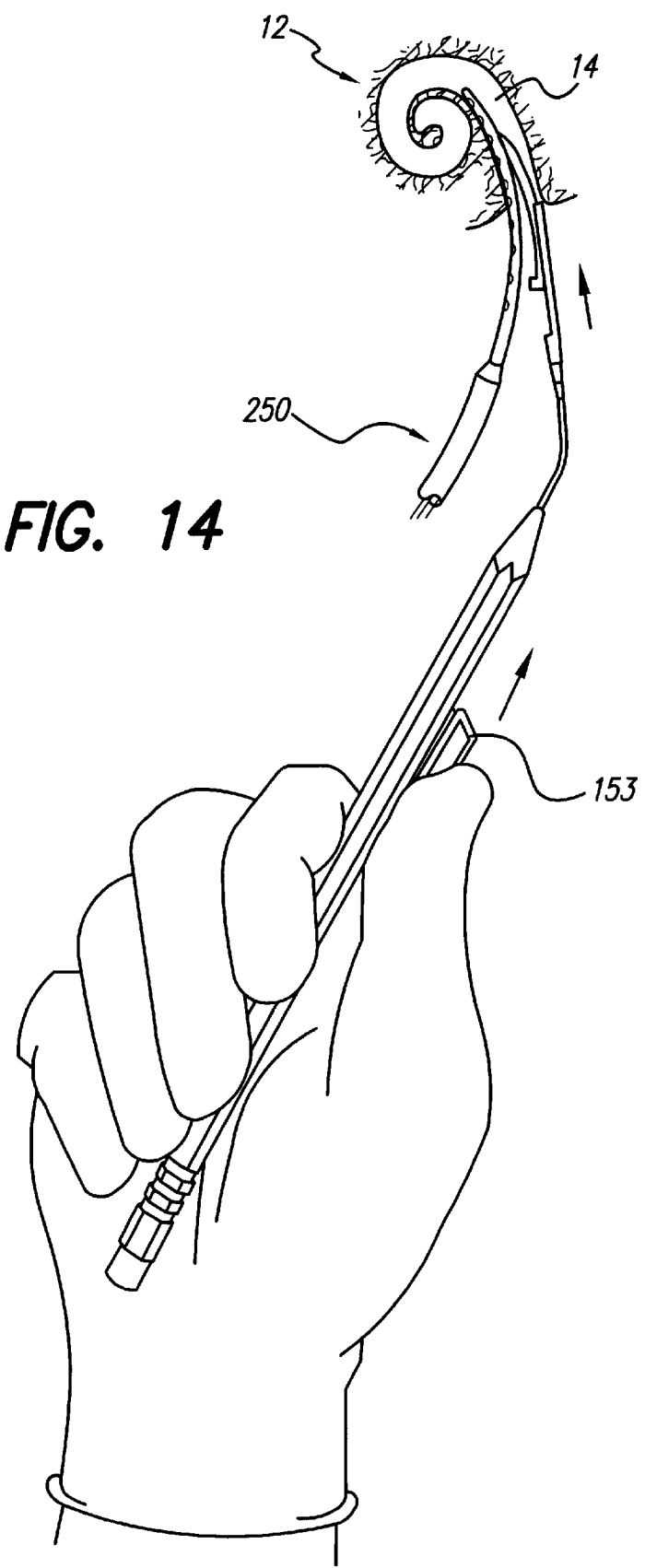
FIG. 14 illustrates the preferred process of inserting the electrode system into the cochlea.

Turning next to FIGS. 13 and 14, a preferred manner of inserting the electrode system 250 into the scala tympani 14 of the cochlea 12 is illustrated. Such insertion is facilitated using an insertion tool 150. Essentially, the insertion tool 150 includes an extendable stylet wire 154, as well as an extendable pushing/guiding tube 152, controlled by a sliding handle or knob 153. Further details associated with the insertion tool 150 are found in Applicant's copending patent application, Ser. No. 09/216,063, now U.S. Pat. No. 6,078,841 previously referenced and incorporated herein by reference.

As seen in FIG. 13, the physician or other medical personnel grasps the electrode assembly near the distal end between a thumb and a forefinger. While held in this position, the stylet wire of the insertion tool 150 is threaded all the way into the channel 27 that passes longitudinally through the positioner 20.

Then, as illustrated in FIG. 14, the distal end of the electrode system 250 is steered into the basal end of the scala tympani duct 14 of the cochlea 12, using the pushing/guiding tube 152, as needed, to help guide the insertion. Once the distal tip of the electrode system 250 is inserted into the cochlea, then the physician simply moves the handle or tab 153 on the tool, which causes the stylet wire 154 to be extended forward a controlled distance. This controlled distance is set to be equal to the desired insertion depth of the electrode system 250 within the cochlea. Hence, as the stylet wire 154 is extended, the positioner 20 is pushed into the cochlea to the desired insertion depth. As the positioner 20 is thus pushed into the cochlea, the electrode array 30' is carried with it, due to the attachment of the positioner to the electrode array at the distal end of the assembly.

Figure 15:
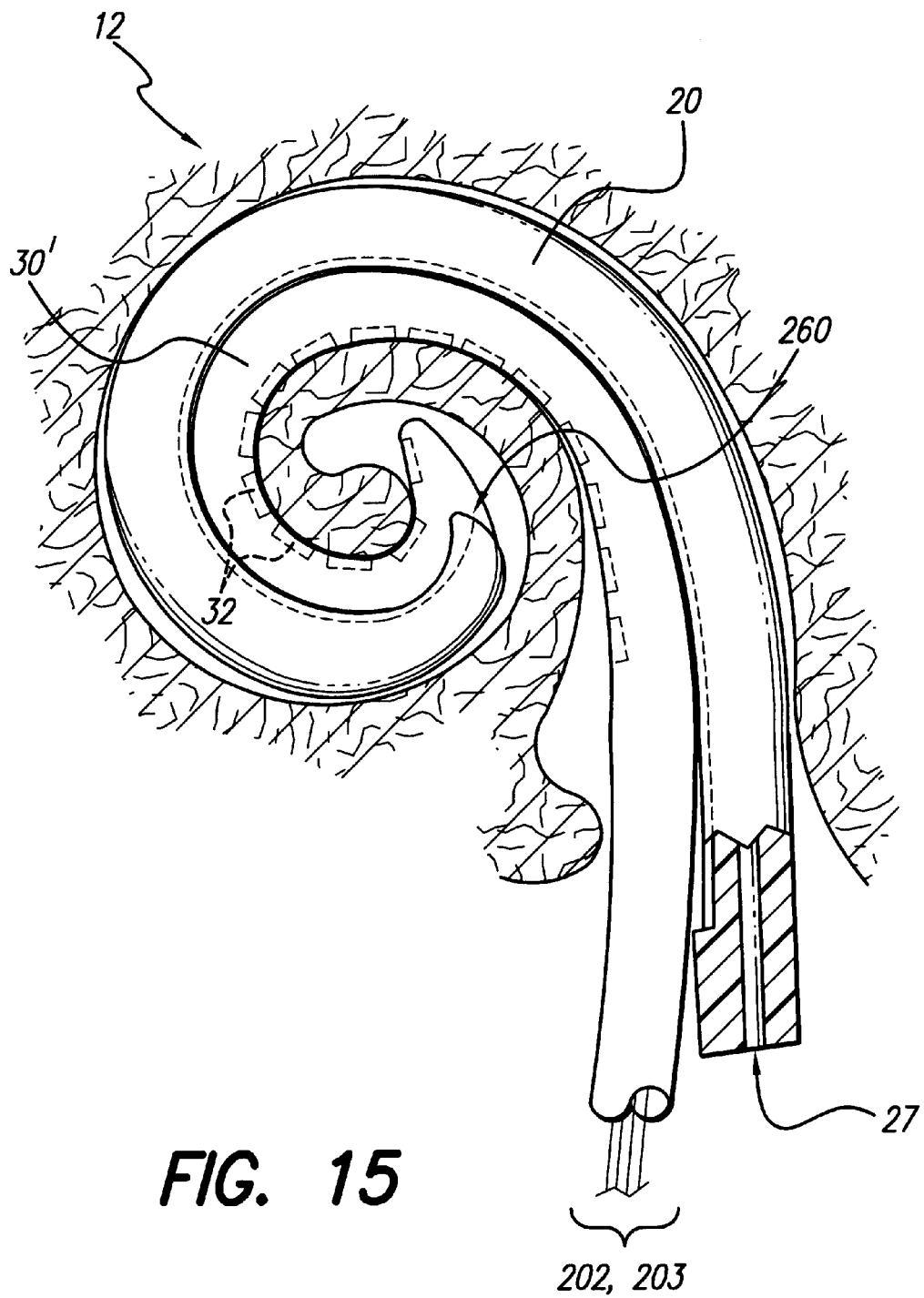
FIG. 15 shows the electrode system of the present invention inserted into the cochlea.

Hence, as shown in FIGS. 13 and 14, it is seen that through a single operation, i.e., extending the stylet wire 154 a prescribed amount, both the electrode array 30' and the positioner 20 are inserted into the cochlea 12 at the same time. When fully inserted, as shown in FIG. 15, both the electrode array 30' and the positioner 20, reside in their desired orientation within the cochlea 12, with the electrode contacts 32 of the electrode array 30' hugging the modiolar wall, and with the positioner 20 filling the space behind the electrode array so as to force the electrode array snugly against the modiolar wall. When the electrode system 250 is thus fully inserted, the stylet wire is removed from the longitudinal channel 27 of the positioner.

Advantageously, the entire process of inserting the electrode system 250 into the cochlea, as illustrated in FIGS. 13–15, can take place in a very short time once the tip of the assembly has been steered into the basal end of the scala tympani of the cochlea. Further, during the actual insertion process, the distal tip of the electrode array, which leads the assembly as it slides into the cochlea, acts as a bumper and guides the assembly deep into the cochlea, through the various spiraling turns of the cochlea, without damaging or causing other significant trauma to the inside of the cochlea. For this reason, the carrier of the electrode array 30', in accordance with the present invention, may be made entirely of a relatively soft material, e.g., LSR 25. Such material is a softer and more pliable material than has heretofore been used for the carrier of the electrode array 30' when the electrode array must be inserted into the cochlea by itself without being an integral part of an electrode assembly.

As described above, it is thus seen that the electrode system of the present invention assures that the electrode contacts of the electrode array are optimally positioned facing the medial direction, e.g., facing the modiolar wall in a cochlea of any size or any side (left or right) of the body. Moreover, the electrode system assures the electrode contacts, or alternatively the non-conductive humps or bumps (if used) between the electrode contacts, are positioned against the modiolar wall. Additionally, it is seen that the electrode system may be manufactured using easy, low cost technology; and once assembled, may be easily inserted into the cochlea, and removed and reinserted, if required. Finally, it is seen that the invention provides a space-filling electrode system for use in the cochlea that may be readily inserted into the cochlea with minimal effort and without risk of undue injury, harm or trauma to the cochlea.

While the invention herein disclosed has been described by means of specific embodiments and applications thereof, numerous modifications and variations could be made thereto by those skilled in the art without departing from the scope of the invention set forth in the claims.

What is claimed is:

1. An implantable electrode system for use with a tissue stimulation device comprising an electrode array and a positioner, the electrode array and the positioner being joined together near their distal end but not joined anywhere else, wherein:

the electrode array comprises:
a flexible carrier having a medial side,
a multiplicity of electrodes on the flexible carrier having an exposed surface area, and
a multiplicity of wires embedded within the flexible carrier, at least one wire of the multiplicity of wires being electrically and physically connected to a respective electrode; and wherein the positioner comprises:
an elongate silastic member having a tapered cross section, with a distal tip of the positioner having a smaller cross section than a proximal end of the positioner,
the positioner having a length which allows the distal tip of the positioner to be inserted into the cochlea to a depth of about 1 to 1½ turns when the proximal end is at the opening of the cochlea,
wherein the cross sectional size of the positioner fills only a fraction of the available space within the cochlea, whereby the electrode array may jointly occupy the space within the cochlea with the positioner, and
wherein the positioner includes a lumen that passes longitudinally through the elongate silastic member.

2. The implantable electrode system of claim 1 wherein the distal tip of the positioner is joined to the electrode array near, but not at, the distal tip of the electrode array.

3. The implantable electrode system of claim 2 further including a pin protruding from the distal tip of the positioner, and an adhesive that bonds the distal tip of the positioner to the electrode array, wherein the pin protrudes into the adhesive.

4. The implantable electrode system of claim 3 wherein the adhesive comprises a biocompatible silastic adhesive.

5. The implantable electrode system of claim 2 wherein the distal tip of the positioner is joined to the electrode array approximately 3 to 4 mm from the distal tip of the electrode array.

6. The implantable electrode system of claim 1 wherein the positioner further includes a channel along one side of the positioner into which the electrode array may reside.

7. The implantable electrode system of claim 6 wherein the positioner further includes a tab at the proximal end of the positioner on the same side of the positioner as the channel.

8. The implantable electrode system of claim 1 wherein the multiplicity of electrodes in the electrode array reside on the medial side electrode array.

9. The implantable electrode system of claim 8 wherein each electrode of the electrode array comprises first and second metallic strips formed in a "T" shape, wherein a leg of the "T" is folded and holds at least one of the multiplicity of wires, the wire being electrically bonded to the folded T leg, and wherein sides of the "T" are folded upwardly into the flexible carrier.

10. The implantable electrode system of claim 9 wherein the folded up sides of the "T" form a "Δ" shape, the folded up sides of the "Δ" comprising an embedded portion of the electrode, and wherein the multiplicity of wires are grouped into first and second wire bundles, the first wire bundle passing through one side of the "Δ", and the second wire bundle passing through the other side of the "Δ".

11. The implantable electrode system of claim 8 further including a tip at the distal end of the electrode array made from a material that is softer than the flexible carrier.

12. The implantable electrode system of claim 8 further including a hump formed on the medial side of the electrode array in the space between the electrodes.

13. The implantable electrode system of claim 8 wherein the electrode array comprises an implantable cochlear electrode array adapted for insertion into a cochlea of a patient, and wherein each electrode has an exposed contact surface area that is rectangular in shape.

14. An implantable cochlear electrode system for use with a cochlear stimulation system comprising a cochlear electrode array and a positioner, the cochlear electrode array and the positioner being joined together near their respective distal ends but not joined anywhere else, the positioner comprising an elongate silastic member having a longitudinal channel passing therethrough, the longitudinal channel being closed at the distal end of the positioner.

15. The implantable cochlear electrode system of claim 14 wherein the cochlear electrode array comprises an elongate silastic carrier and a multiplicity of spaced-apart electrode contacts distributed along a medial side of the elongate silastic carrier, the elongate silastic carrier having a multiplicity of wires embedded therein, wherein at least one wire of the multiplicity of wires makes electrical contact with each electrode contact.

16. The implantable cochlear electrode system of claim 15 wherein at least eight spaced-apart electrodes are embedded within the elongate silastic carrier, each electrode having an exposed surface area only on the medial side of the flexible carrier; and wherein the electrode array is more flexible in a medial direction than in a lateral direction, where the medial direction comprises a direction perpendicular to the medial side, and where the lateral direction comprises a direction perpendicular to the medial direction and the longitudinal axis.

17. The implantable cochlear electrode system of claim 16 further including a hump formed in the space between the exposed contact surface area of each electrode.

18. The implantable cochlear electrode system of claim 15 wherein the elongate silastic carrier has a natural curve in the medial direction.

* * * * *